US006887893B1

(12) United States Patent
Kurakata et al.

(10) Patent No.: US 6,887,893 B1
(45) Date of Patent: May 3, 2005

(54) METHODS AND COMPOSITIONS FOR TREATMENT AND PREVENTION OF TUMORS, TUMOR-RELATED DISORDERS AND CACHEXIA

(75) Inventors: Shinichi Kurakata, Yokohama (JP); Masaharu Hanai, Tokyo (JP); Saori Kanai, Sakura (JP); Tomio Kimura, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 101 days.

(21) Appl. No.: 09/212,556

(22) Filed: Dec. 16, 1998

(30) Foreign Application Priority Data

| Dec. 24, 1997 | (JP) | 9-354499 |
| Jan. 28, 1998 | (JP) | 10-15306 |
| Jul. 21, 1998 | (JP) | 10-204907 |
| Sep. 24, 1998 | (JP) | 10-269444 |

(51) Int. Cl.$^7$ .................. A61K 31/40; C07D 405/00
(52) U.S. Cl. .................. 514/427; 514/422; 548/517; 548/526; 548/562; 548/563
(58) Field of Search .................. 514/427, 422; 548/517, 526, 562, 563

(56) References Cited

U.S. PATENT DOCUMENTS

| 5,208,018 A | 5/1993 | Gough |
| 5,317,019 A | 5/1994 | Bender et al. |
| 5,344,991 A | 9/1994 | Reitz et al. |
| 5,380,738 A | 1/1995 | Norman et al. |
| 5,418,254 A | 5/1995 | Huang et al. |
| 5,474,995 A | 12/1995 | Ducharme et al. |
| 5,486,534 A | 1/1996 | Lee et al. |
| 5,521,207 A | 5/1996 | Graneto |
| 5,593,991 A | 1/1997 | Adams et al. |
| 5,616,601 A | 4/1997 | Khanna et al. |
| 5,620,999 A | 4/1997 | Weier et al. |
| 5,633,272 A | 5/1997 | Talley et al. |
| 5,908,858 A | 6/1999 | Kimura et al. |
| 5,932,598 A | 8/1999 | Talley et al. |

FOREIGN PATENT DOCUMENTS

| CA | 2180624 A | 1/1997 |
| EP | 799823 A | 10/1997 |
| EP | 0799823 | * 10/1997 |
| WO | WO 94/15932 | 7/1994 |
| WO | WO 94/27980 | 12/1994 |
| WO | WO 95/00501 | 1/1995 |
| WO | WO 95/02600 | 1/1995 |
| WO | WO 95/11883 | 5/1995 |
| WO | WO 95/15316 | 6/1995 |
| WO | WO 95/30656 | 11/1995 |
| WO | WO 96/03385 | 2/1996 |
| WO | WO 96/03387 | 2/1996 |
| WO | WO 96/03388 | 2/1996 |
| WO | WO 96/25405 | 8/1996 |
| WO | WO 96/36617 | 11/1996 |
| WO | WO 96/38418 | 12/1996 |
| WO | WO 97/13755 | 4/1997 |
| WO | WO 97/27181 | 7/1997 |
| WO | WO 97/38986 | 10/1997 |
| WO | WO 98/16227 | 4/1998 |
| WO | WO 98/22101 | 5/1998 |
| WO | WO 98/25896 | 6/1998 |

OTHER PUBLICATIONS

Mayo Clinic, Acetaminophen, (Print of Web Article from MayoClinic.com), Nov. 22, 2002.*
Ruff et al., Journal of Clinical Investigat., vol. 73, pp. 1483–1486.*
X. Lu et al, "NSAID–Induced Apoptosis in Rous Sarcoma Virus–Transformed Chicken Embryo Fibroblasts is Dependent on v–srv and c–myc and is Inhibited by bcl–2", *Prostaglandins*, vol. 54, pp. 549–568 (Aug. 1997).
T. Hla et al, "Role of the Early Response Gene Cyclooxygenase (COX) –2 in Angiogenesis", *Molecular, Cellular, and Clinical Aspects of Angiogenesis*, Edited by M.E. Maragoudakis, Plenum Press, Nato ASI Series, Series A: Life Series, vol. 285, pp. 191–198 (1966).
N. Yoshimi et al, "Inhibitory Effect of NS–398, a Selective Cyclooxygenase–2 Inhibitor, on Azoxymethane–induced Aberrant Crypt Foci in Colon Carcinogenesis of F344 Rats", *Jpn. J. Cancer Res.*, vol. 88, pp. 1044–1051 (Nov. 1997).
N. Rioux et al, "Recovery from 4–(methylInitrosamino) – 1–(3–pyridyl) –1–butanone–Induced Immunosuppression in A/J Mice by Treatment With Nonsteroidal Anti–inflammatory Drugs", *J. Natl. Cancer Inst.*, vol. 89, No. 12, pp. 874–880 (Jun. 1997).
K. K. Wu, "Cyclooxygenase 2 Induction: Molecular mechanism and pathophysiologic roles", *J. Lab. Clin. Med.*, vol. 128, No. 3, pp. 242–245 (1996).
H. Sheng et al, "Inhibition of Human Colon Cancer Cell Growth by Selective Inhibition of Cyclooxygenase–2", *J. Clin. Invest.*, vol. 99, No. 9, pp. 2254–2259 (May 1997).
M. Takahashi et al, "Suppression of azoxymethane–induced aberrant crypt focl in rat colon by nimesulide, a selective Inhibitor of cyclooxygenase 2",*J. Cancer Res. Clin. Oncol.*, vol. 122, pp. 219–222 (1996).
M. L. Parrett et al, "Cyclooxygenase–2 gene expression in human breast cancer", *Int. J. Oncol.*, vol. 10, pp. 503–507 (1997).
H.A. Lehmann et al, "Meloxicam: A Toxicology Overview", *Inflammopharmacology*, vol. 4, pp. 105–123, Kluwer Academic Publishers (1996).
M. Katori, "Solid tumor, plasma exudation arachidonic acid metabolism", *Igaku no Ayumi*, vol. 175, No. 8, pp. 527–531 (1995).

(Continued)

Primary Examiner—James O. Wilson
Assistant Examiner—Howard V. Owens, Jr.
(74) Attorney, Agent, or Firm—Frishauf, Holtz, Goodman & Chick, P.C.

(57) ABSTRACT

Certain cyclooxygenase-2 inhibitors are useful for the treatment and prevention of tumors and tumor-related disorders and cachexia.

8 Claims, No Drawings

OTHER PUBLICATIONS

G. G. Sheng et al, "A Selective Cyclooxygenase 2 Inhibitor Suppresses the Growth of H–ras–Transformed Rat Intestinal Epithelial Cells", *Gastroenterology*, vol. 113, No. 6, pp. 1883–1891 (Dec. 1997).

P. Huang et al, "Cyclooxygenase and 5–lipoxygenase inhibitors for the prevention and treatment of cancer", Oncologic, Endocrine & Metabolic—Monthly Update, *Exp. Opin. Invest. Drugs*, vol. 4, No. 3, pp. 243–249 (1995).

D. J. E. Elder et al, "Induction of Apoptotic Cell Death in Human Colorectal Carcinoma Cell Lines by a Cyclooxygenase–2 (COX) –2 –selective Nonsteroidal Anti–Inflammatory Drug: Independence from COX–2 Protein Expression", *Clin. Cancer Res.*, vol. 3, pp. 1679–1683 (Oct. 1997).

M. Tsujii et al, "COX–2 . . . ", *Chirougaku*, vol. 30, No. 12, pp. 1401–1405 (1996).

M. Tsujii et al, Alterations in Cellular Adhesion and Apoptosis in Epithelial Cells Overexpressing Prostaglandin Endoperoxide Synthase 2, *Cell*, vol. 83, pp. 493–501 (1995).

D. DeWitt et al, "Yes, but Do They Still Get Headaches?", *Cell*, vol. 83, pp. 345–348 (1995).

P. K. Lala et al, "Effects of Chronic Indomethacin Therapy on the Development and Progression of Spontaneous Mammary Tumors in C3H/HEJ Mice", *Int. J. Cancer*, vol. 73, pp. 371–380 (1997).

B. S. Reddy et al, "Evaluation of Cyclooxygenase–2 Inhibitor for Potential Chemopreventive Properties in Colon Carcinogenesis", *Cancer Res.*, vol. 56, pp. 4566–4569 (1996).

I. K. Khanna et al, "1, 2–Diarylimidazoles as Potent, Cyclooxygenase–2 Selective, and Orally Active Antiinflammatory Agents", *J. Med. Chem.*, vol. 40, pp. 1634–1647 (1997).

I. K. Khanna et al, "1, 2–Diarylpyrroles as Potent and Selective Inhibitors of Cyclooxygenase–2", *J. Med. Chem.*, vol. 40, pp. 1619–1633, (1997).

McCarthy, "Inhibitors of Prostaglandin Synthesis Do Not Improve Food Intake or Body Weight of Tumor–Bearing Rats", *Research in Nursing & Health*, 1999, pp. 380–387, vol. 22).

Malmberg, et al., Capsaicin–evoked prostaglandin $E_2$ release in spinal cord slices : relative effect of cyclooxygenase inhibitors, *Eur. J. Pharmacol.*, 271, 293–299 (1994).

Ferrari, et al., estimation of the in vivo effect of cyclooxygenase inhibitors on prostaglandin $E_2$ levels in mouse brain, *Eur. J. Pharmacol.*, 179, 25–34 (1990).

Shaffer, et al., "Attenuation by Acetaminophen of Arachidonic Acid–Induced Coronary Vasodilation and Output of Prostaglandins in the Isolated Rat Heart", *Eur. J. pharmacol.*, 72, 57–61 (1981).

Mattammal, et al., "Mechanism of Inhibition of Renal Prostaglandin Production by Acetaminophen", *J. Pharmacol. Exp. Ther.*, 210, 405–409 (1979).

Damas, et al., "Inhibition De L'Action Hypotensive De L'Acide Arachindonique Chez Le Rat", *J. Pharmacol. (Paris)*, 9, 1, 13–23 (1978).

Zenser, et al., "Effect of Acetaminophen on Prostaglandin $E_2$ and Prostaglandin $F_{2\alpha}$ Synthesis in the Renal Inner Medulla of Rat", *Biochim. Biophys. Acta*, 542, 486–495 (1978).

\* cited by examiner

METHODS AND COMPOSITIONS FOR TREATMENT AND PREVENTION OF TUMORS, TUMOR-RELATED DISORDERS AND CACHEXIA

BACKGROUND TO THE INVENTION

The present invention relates to the use of certain compounds, specifically cyclooxygenase-2 inhibitors (hereinafter referred to as "COX-2 inhibitors") for the treatment and prevention of tumors and tumor-related disorders and cachexia.

Cachexia is a systemic disease of which the cardinal symptoms are progressive weight loss, anemia, edema, loss of appetite and so forth. It may occur as a side-effect of certain chronic diseases, such as malignant tumors, tuberculosis, diabetes, blood diseases, endocrine diseases, infections and acquired immune deficiency syndrome. When cachexia occurs as a result of the presence of a malignant tumor, even if the administration of antitumor drugs to the patient with malignant tumor is effective and antitumor effects are experienced, there is normally no improvement in the cachexia because of adverse effects such as the myelotoxicity which may be caused by the antitumor drug.

The treatment of cachexia is often very difficult for the following reasons:

Since the strength of a patient is greatly depleted as cachexia progresses, it may become impossible to continue treatment using antitumor drugs (which generally exhibit a high level of toxicity), and this thereby becomes an obstacle to the treatment of the malignant tumor.

Nutritional supplements are often given in order to treat the symptoms of cachexia. This, however, often enhances the progress of the malignant tumor, and may shorten the survival time of the patient.

At present, no satisfactory treatment for cachexia has been established, and there is an increasing need for agents that alleviate the symptoms of cachexia.

The compounds of formula (I) or (II), shown below, which, with certain other compounds, are the active ingredients of the compositions of the present invention, are known to inhibit selectively cyclooxygenase-2 (COX-2). They are also known to inhibit the production of inflammatory cytokines (particularly IL-1 and TNF-α), to inhibit the production of leukotrienes (particularly $LTB_4$), to inhibit bone resorption, and to have analgesic, anti-inflammatory and anti-pyretic effects (European Patent Publication No. 799 823A).

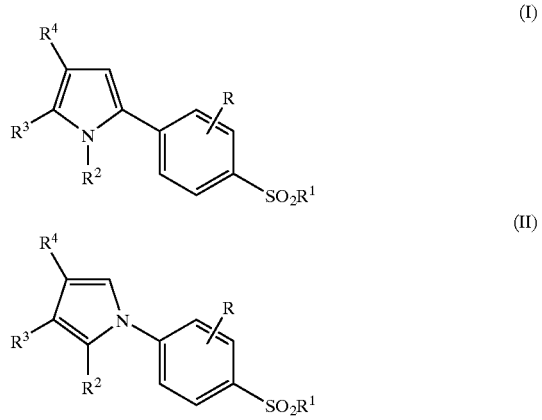

It has not previously been known that these compounds can be used for the treatment or prevention of cachexia.

Also, although it is known that certain other active ingredients employed in the present invention, namely the compounds of formula (III), (IV), (V), (VI), (VII), (VIII), (IX), (X), (XI), (XII), (XIII) and (XIV) have selective inhibitory activity against cyclooxygenase-2, an inhibitory effect on the production of inflammatory cytokines (particularly IL-1 and TNF-α), an inhibitory action on the production of leukotrienes (particularly $LTB_4$), an inhibitory action on bone resorption, an analgesic action, an anti-inflammatory action and an antipyretic action [International publication number WO95/00501, J. Med. Chem., 40, 1347 (1997), International publication number WO94/13635, Pharmacology, 55, 44 (1997), Prostaglandins, 47, 55 (1994), Japanese publication number Hei 9-52882, Jpn. J. Pharmacol., 67,305 (1995), Inflamm. Res., 47, Suppl. 3, S257 (1997), J. Med. Chem., 38, 4570 (1995), U.S. Pat. No. 5,474,995, European Patent No. 863 134 and International Patent Publication No. WO 98/06708], it has not previously been disclosed that these compounds have an effect against cachexia.

It is known from epidemiological studies that the taking of conventional NSAIDS (non-steroidal anti-inflammatory drugs, which are COX-1 and COX-2 inhibitors), the most common of which is aspirin, and the incidence of colon cancer have an inverse correlation. In addition, there have been many reports that NSAIDS, such as aspirin and sulindac, have shown inhibitory activity against tumor metastasis and carcinogenesis in preclinical studies. Some NSAIDS have been used in clinical studies for the prevention of colon carcinogenesis.

However, since conventional NSAIDS are not selective for COX-1 or COX-2, the occurrence of adverse effects is unavoidable.

It would, therefore, be desirable to discover a selective cyclooxygenase-2 inhibitor (selective COX-2 inhibitor) for use as an anti-tumor agent that has a low level of adverse effects.

Among the known selective COX-2 inhibitors, it is known that MF-tricyclic [Oshima, M. et al. "Suppression of Intestinal Polyposis in APCΔ[716] Knockout Mice by Inhibition of Cyclooxygenase 2 (COX-2)", Cell, 87, 803–809 (1996)] and celecoxib (Reddy, R. S. et al. "Evaluation of Cyclooxygenase-2 Inhibitor for Potential Chemopreventive Properties in colon Carcinogenesis", Cancer Res., 56, 4566–4569 (1996)] inhibit the occurrence of experimental colonic polyposis, and that SC-58125 exhibits growth inhibitory effects against certain types of human colon cancer cell lines (Sheng, H. et al. "Inhibition of Human Colon Cancer Cell Growth by Selective Inhibition of Cyclooxygenase-2", J. Clin. Invest., 99, 2254–2259(1997)].

However, in the case of the former, the experimental system used is not a model for an established colon cancer, and the compounds are only able to prevent the occurrence of polyposis in the preliminary stage of colon cancer.

On the other hand, with respect to the latter, the only colon cancer cell line in which growth inhibitory effects against human colon cancer cell lines have been observed is a cell line that expresses cyclooxygenase-2 (human colon cancer cell line HCA-7), and it has been disclosed that colon cancer cell lines that do not exhibit tumor growth inhibitory activity (HCT-116) in vitro do not exhibit tumor growth inhibitory effects in vivo. Thus, whether or not COX-2 inhibitor-induced tumor growth inhibitory effects on colon cancer are expressed in vivo depends on the sensitivity of the colon cancer cell lines used against COX-2 inhibitor-induced cell growth inhibitory activity in vitro. It is thus unlikely that the tumor growth inhibitory effects of COX-2 inhibitors in vivo would be observed against various other cancers, especially those cancers, including colon cancers, that are resistant to COX-2 inhibitor-induced inhibition of cell growth in vitro and that do not express cyclooxygenase-2.

Moreover, there has been no previous disclosure of the use of a combination of a selective cyclooxygenase-2 inhibitor and a 5-fluorouracil derivative for the prevention or inhibition of tumor growth.

We have now found that certain 1,2-diphenylpyrrole derivatives and closely related compounds have excellent activity for the prevention or inhibition of cachexia, and that these 1,2-diphenylpyrrole derivatives are effective for the treatment or prevention of tumor-related disorders, alone or in combination with a 5-fluorouracil derivative.

BRIEF SUMMARY OF THE INVENTION

Thus, in a first embodiment, the present invention provides a method for the treatment or prevention of cachexia in a mammal, which may be human, in need of such treatment or prevention, which method comprises administering to said mammal an effective amount of an active compound selected from the group consisting of compounds of formula (I), (II), (III), (IV), (V), (VI), (VII), (VIII), (IX), (X), (XI), (XII), (XIII) and (XIV):

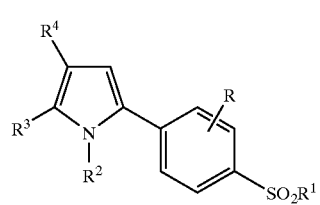
(I)

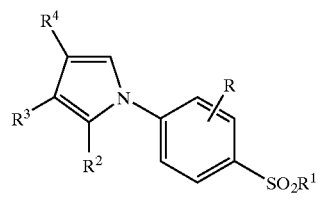
(II)

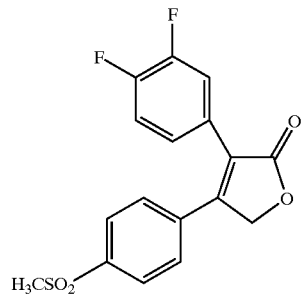
(III)

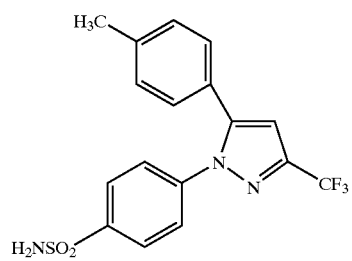
(IV)

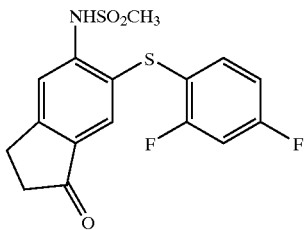
(V)

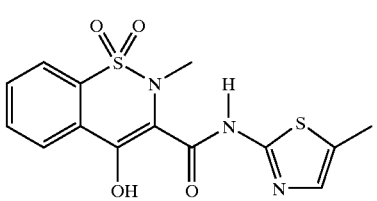
(VI)

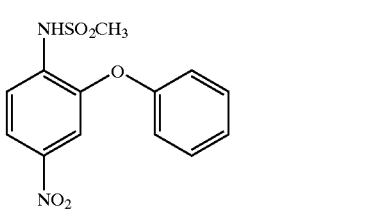
(VII)

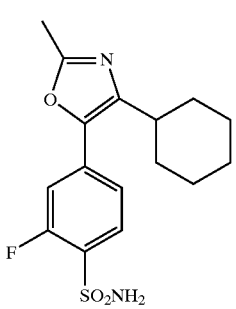
(VIII)

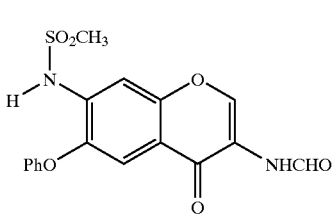
(IX)

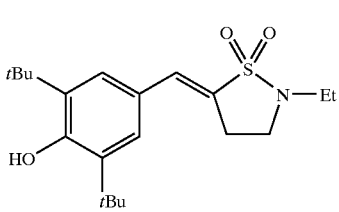
(X)

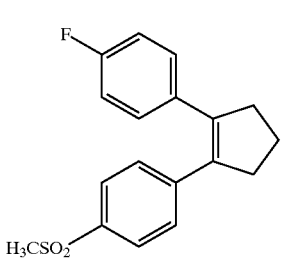
(XI)

-continued

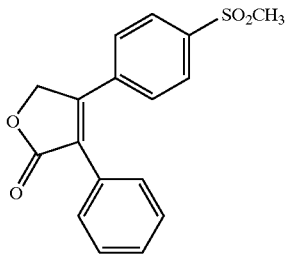

(XII)

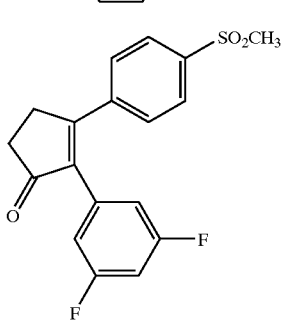

(XIII)

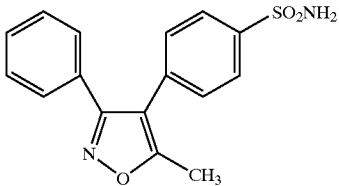

(XIV)

wherein

R represents a hydrogen atom, a halogen atom or a lower alkyl group;

$R^1$ represents a lower alkyl group, an amino group or a group of formula —$NHR^a$ (wherein $R^a$ represents a group which may be eliminated in vivo);

$R^2$ represents a phenyl group or a phenyl group having at least one substituent selected from the group consisting of substituents α and substituents β, defined below;

$R^3$ represents a hydrogen atom, a halogen atom, a lower alkyl group or a lower alkyl group having at least one substituent selected from the group consisting of substituents α;

$R^4$ represents a hydrogen atom, a lower alkyl group, a lower alkyl group having at least one substituent selected from the group consisting of substituents α, a cycloalkyl group, an aryl group as defined below, or an aralkyl group as defined below;

said aryl group is a carbocyclic aromatic hydrocarbon group having from 6 to 14 carbon atoms in one or more aromatic rings or such a group which is fused to a cycloalkyl group having from 3 to 10 carbon atoms, and the group is unsubstituted or it is substituted by at least one substituent selected from the group consisting of substituents α and substituents β;

said aralkyl group is a lower alkyl group which is substituted by one or more of the aryl groups defined above;

tBu represents a t-butyl group;

Et represents an ethyl group; and

Ph represents a phenyl group;

said substituents α are selected from the group consisting of hydroxy groups, halogen atoms, lower alkoxy groups and lower alkylthio groups; and said substituents β are selected from the group consisting of lower alkyl groups, alkanoyloxy groups, mercapto groups, alkanoylthio groups, lower alkylsulfinyl groups, lower alkyl groups having at least one substituent selected from the group consisting of substituents α, cycloalkyloxy groups, lower haloalkoxy groups and lower alkylenedioxy groups;

and pharmaceutically acceptable salts thereof.

The invention further provides a method for the treatment or prevention of tumor-related disorders in a mammal, which may be human, in need of such treatment or prevention, which method comprises administering to said mammal an effective amount of an active compound selected from the group consisting of compounds of formula (I) and (II), defined above.

DETAILED DESCRIPTION OF INVENTION

Preferred classes of compounds of the present invention are those compounds of formula (I) and (II) in which:

(1) R represents a hydrogen atom, a fluorine atom, a chlorine atom or a methyl group, more preferably the hydrogen atom, (2) $R^1$ represents a methyl group, an amino group or an acetylamino group, more preferably the amino group or acetylamino group, (3) $R^2$ represents a phenyl group or a phenyl group having at least one substituent selected from the group consisting of substituents $α^1$ and substituents $β^1$, more preferably a phenyl group or phenyl group having at least one substituent selected from the group consisting of substituents $α^1$ and substituents $β^2$, still more preferably a phenyl group in which the number of substituents is from 1 to 3, (4) $R^3$ represents a hydrogen atom, a halogen atom, a lower alkyl group or a lower alkyl group having at least one substituent selected from the group consisting of substituents $α^1$, more preferably a hydrogen atom, a halogen atom, a lower alkyl group or a lower alkyl group substituted with a halogen atom, (5) $R^4$ represents a hydrogen atom, a lower alkyl group, a lower alkyl group having at least one substituent selected from the group consisting of substituents α, a cycloalkyl group, an aryl group, an aryl group having at least one substituent selected from the group consisting of substituents $α^1$ and substituents $β^3$, an aralkyl group or an aralkyl group having at least one substituent selected from the group consisting of substituents $α^1$ and substituents $β^3$, more preferably a hydrogen atom, a lower alkyl group, a lower alkyl group having at least one substituent selected from the group consisting of substituents $α^2$, a cycloalkyl group, an aryl group, an aryl group having at least one substituent selected from the group consisting of substituents $α^2$ and substituents $β^4$, an aralkyl group or an aralkyl group having at least one substituent selected from the group consisting of substituents $α^2$ and substituents $β^4$.

Said substituents $α^1$ are selected from the group consisting of halogen atoms, lower alkoxy groups and lower alkylthio groups.

Said substituents $α^2$ are selected from the group consisting of hydroxy groups, halogen atoms and lower alkoxy groups.

Said substituents $β^1$ are selected from the group consisting of lower alkyl groups, mercapto groups, alkanoylthio groups, lower alkyl groups having at least one substituent selected from the group consisting of substituents $α^1$, lower haloalkoxy groups and lower alkylenedioxy groups.

Said substituents $β^2$ are selected from the group consisting of lower alkyl groups, mercapto groups, alkanoylthio groups, lower alkyl groups substituted with a halogen atom, lower haloalkoxy groups and lower alkylenedioxy groups.

Said substituents $\beta^3$ are selected from the group consisting of lower alkyl groups, lower alkyl groups having at least one substituent selected from the group consisting of substituents $\alpha$ and cycloalkyloxy groups.

Said substituents $\beta4$ are selected from the group consisting of lower alkyl groups, lower alkyl groups substituted with a halogen atom and cycloalkyloxy groups.

In the compounds of formula (I) and (II), where R, $R^3$, substituents $\alpha$, substituents $\alpha^1$ or substituents $\alpha^2$ represents a halogen atom, or where substituents $\beta^2$ or substituents $\beta^4$ represents a lower alkyl group substituted with halogen atom, the halogen atom is preferably a fluorine atom, a chlorine atom, a bromine atom or an iodine atom, preferably a fluorine atom, a chlorine atom or a bromine atom.

Where R, $R^1$, $R^3$, $R^4$, substituent $\beta$, substituent $\beta^1$, substituent $\beta^2$, substituent $\beta^3$ or substituent $\beta^4$ represents a lower alkyl group, or $R^3$, $R^4$, substituent $\beta$, substituent $\beta^1$ or substituent $\beta^3$ represents a lower alkyl group having at least one substituent selected from the group consisting of substituents $\alpha$, or substituent $\beta^2$ or substituent $\beta^4$ represents a lower alkyl group substituted with a halogen atom, the alkyl group or alkyl part of the substituted group may be a straight or branched chain alkyl group having from 1 to 6 carbon atoms, and examples include the methyl, ethyl, propyl, isopropyl, butyl, isobutyl, sec-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. Of these, we prefer the straight or branched chain alkyl groups having from 1 to 4 carbon atoms, more preferably the methyl and ethyl groups. In R, $R^1$ and $R^4$, the lower alkyl group is particularly preferably the methyl group.

Where substituent $\beta$ represents an alkanoyloxy group, or substituent $\beta$, substituent $\beta^1$ or substituent $\beta^2$ represents an alkanoylthio group, the alkanoyl part of these groups may be, for example, a straight or branched chain alkanoyl group having from 1 to 25 carbon atoms, such as the formyl, acetyl, propionyl, butyryl, isobutyryl, valeryl, isovaleryl, pivaloyl, hexanoyl, heptanoyl, octanoyl, nonanoyl, decanoyl, undecanoyl, lauroyl, tridecanoyl, myristoyl, palmitoyl, stearoyl, icosanoyl, docosanoyl and pentacosanoyl groups. Of these, we prefer those alkanoyl groups having from 1 to 12 carbon atoms, more preferably those alkanoyl groups having from 1 to 6 carbon atoms, still more preferably those alkanoyl groups having from 1 to 4 carbon atoms, and most preferably the acetyl and propionyl groups.

Where $R^4$ represents a cycloalkyl group, this is preferably a cycloalkyl group having from 3 to 8 carbon atoms, such as the cyclopropyl, cyclobutyl, cyclopentyl, cyclohexyl, cycloheptyl and cyclooctyl groups. Of these, we prefer those cycloalkyl group having from 3 to 7 carbon atoms, more preferably those cycloalkyl groups having from 3 to 6 carbon atoms, and most preferably the cyclopropyl group.

Where $R^4$ represents an aryl group, this aryl group may be a carbocyclic aromatic hydrocarbon group having from 6 to 14 carbon atoms and may be unsubstituted or it may be substituted by at least one substituent selected from the group consisting of substituents $\alpha$ and substituents $\beta$. The group may contain a single aromatic ring or it may contain two or more fused rings. Examples of such groups include the phenyl, indenyl, naphthyl, phenanthrenyl and anthracenyl groups. Of these, we prefer the phenyl and naphthyl groups, more preferably the phenyl group. The above-mentioned aryl group may be condensed with a cycloalkyl group having from 3 to 10 carbon atoms and examples of such condensed groups include, for example, the 2-indanyl group.

Where $R^4$ represents an aralkyl group, this is an alkyl group, which may be any of the alkyl groups defined and exemplified above in relation to R etc., and which is substituted by from 1 to 3 aryl groups, as defined and exemplified above. Such a group may be unsubstituted or it may be substituted by at least one of substituents $\alpha$ or $\beta$. Examples of such groups include the benzyl, phenethyl, 3-phenylpropyl, 4-phenylbutyl, 1-naphthylmethyl, 2-naphthylmethyl, diphenylmethyl, triphenylmethyl, 1-naphthyldiphenylmethyl and 9-anthrylmethyl groups. Of these, we prefer an alkyl group having from 1 to 4 carbon atoms which is substituted with one aryl group having from 6 to 10 carbon atoms.

Where substituent $\alpha$, substituent $\alpha^1$ or substituent $\alpha^2$ represents a lower alkoxy group, this may be, for example, a straight or branched chain alkoxy group having from 1 to 6 carbon atoms, such as the methoxy, ethoxy, propoxy, isopropoxy, butoxy, isobutoxy, sec-butoxy, t-butoxy, pentyloxy, isopentyloxy, 2-methylbutoxy, neopentyloxy, 1-ethylpropoxy, hexyloxy, isohexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy or 2-ethylbutoxy groups. Of these, we prefer the straight or branched chain alkoxy groups having from 1 to 4 carbon atoms, more preferably the methoxy and ethoxy groups.

Where substituent $\alpha^1$ or substituent $\alpha^1$ represents a lower alkylthio group, this may be a straight or branched chain alkylthio group having from 1 to 6 carbon atoms, and examples include the methylthio, ethylthio, propylthio, isopropylthio, butylthio, to isobutylthio, sec-butylthio, t-butylthio, pentylthio, isopentylthio, 2-methylbutylthio, neopentylthio, 1-ethylpropylthio, hexylthio, isohexylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio and 2-ethylbutylthio groups. Of these, we prefer the straight or branched chain alkylthio groups having from 1 to 4 carbon atoms, more preferably the methylthio and ethylthio groups.

Where substituent $\beta$ represents a lower alkylsulfinyl group, this may be a straight or branched chain alkylsulfinyl group having from 1 to 6 carbon atoms, such as the methylsulfinyl, ethylsulfinyl, propylsulfinyl, isopropylsulfinyl, butylsulfinyl, isobutylsulfinyl, sec-butylsulfinyl, t-butylsulfinyl, pentylsulfinyl, isopentylsulfinyl, 2-methylbutylsulfinyl, neopentylsulfinyl, 1-ethylpropylsulfinyl, hexylsulfinyl, isohexylsulfinyl, 4-methylpentylsulfinyl, 3-methylpentylsulfinyl, 2-methylpentylsulfinyl, 1-methylpentylsulfinyl, 3,3-dimethylbutylsulfinyl, 2,2-dimethylbutylsulfinyl, 1,1-dimethylbutylsulfinyl, 1,2-dimethylbutylsulfinyl, 1,3-dimethylbutylsulfinyl, 2,3-dimethylbutylsulfinyl and 2-ethylbutylsulfinyl groups. Of these, we prefer the straight or branched chain alkylsulfinyl groups having from 1 to 4 carbon atoms.

Where substituent $\beta$, substituent $\beta^3$ or substituent $\beta^4$ represents a cycloalkyloxy group, this may be, for example, a cycloalkyloxy group having from 3 to 8 carbon atoms, such as the cyclopropyloxy, cyclobutyloxy, cyclopentyloxy, cyclohexyloxy, cycloheptyloxy and cyclooctyloxy groups.

Of these, we prefer the cycloalkyloxy groups having from 3 to 7 carbon atoms, more preferably the cycloalkyloxy groups having 5 or 6 carbon atoms, most preferably the cyclopentyloxy group.

Where substituent β, substituent $β^1$ or substituent $β^2$ represents a lower haloalkoxy group, this is an alkoxy group, which may be as defined and exemplified above in relation to substituent α etc., and which is substituted by at least one halogen atom, such as those defined and exemplified above. Examples of such groups include the fluoromethoxy, difluoromethoxy, trifluoromethoxy, 2-fluoroethoxy, 2-chloroethoxy, 2-bromoethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups. Of these, we prefer those lower haloalkoxy groups having from 1 to 4 carbon atoms, more preferably the fluoromethoxy, difluoromethoxy, trifluoromethoxy, 2-fluoroethoxy, 2-chloroethoxy, 2-bromoethoxy, 3-fluoropropoxy, 4-fluorobutoxy, chloromethoxy, trichloromethoxy and bromomethoxy groups, and most preferably the fluoromethoxy, difluoromethoxy and trifluoromethoxy groups.

Where substituent β, substituent $β^1$ or substituent $β^2$ represents a lower alkylenedioxy group, this may be, for example, a straight or branched chain alkylenedioxy group having from 1 to 6 carbon atoms, such as the methylenedioxy, ethylenedioxy, trimethylenedioxy, tetramethylenedioxy, pentamethylenedioxy, hexamethylenedioxy and propylenedioxy groups. Of these, we prefer those alkylenedioxy groups having from 1 to 4 carbon atoms, more preferably the methylenedioxy and ethylenedioxy groups.

Where substituent $β^2$ or substituent $β^4$ represents a lower alkyl group substituted with a halogen atom, this may be any of the alkyl groups defined and exemplified above in relation to R etc., which is substituted by at least one halogen atom, as also defined and exemplified above. Examples of such groups include the fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, 2-chloroethyl, 3-chloropropyl, bromomethyl, 2-bromoethyl, iodomethyl, 2-iodoethyl, chlorodifluoromethyl and bromodifluoromethyl groups. Of these, we prefer those haloalkyl groups having from 1 to 4 carbon atoms, more preferably the fluoromethyl, difluoromethyl, trifluoromethyl, 2-fluoroethyl, 3-fluoropropyl, 4-fluorobutyl, chloromethyl, trichloromethyl and bromomethyl groups, and most preferably the fluoromethyl, difluoromethyl and trifluoromethyl groups.

Where $R^a$ represents a group to be eliminated in vivo is a group which can be eliminated in the human body under physiological conditions such as hydrolysis, that is a group producing a free amino group (—NH2) from a group of formula —NHR$^a$ (wherein $R^a$ is as defined above). It is easy to determine whether or not the group can be eliminated in vivo by the following test: a compound to be tested is administered orally or intravenously to an experimental animal, such as a rat or mouse, and the body fluid is tested for the presence or absence of the corresponding compound having a free amino group or a pharmaceutically acceptable salt thereof.

Such groups include, for example:

the alkanoyl groups defined and exemplified above in relation to substituent β etc.;

a lower alkoxycarbonyl group, in which the alkoxy group is as defined and exemplified above in relation to substituent α etc., such as the methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl and cyclohexyloxycarbonyl groups;

an aralkyloxycarbonyl group in which the aryl is as defined above and is unsubstituted or is substituted by one or two lower alkoxy or nitro groups, such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups;

an alkanoyloxymethyl group in which the alkanoyl group is as defined and exemplified above in relation to substituent βetc., such as the formyloxymethyl, acetoxymethyl, propionyloxymethyl, butyryloxymethyl, pivaloyloxymethyl, valeryloxymethyl, isovaleryloxymethyl and hexanoyloxymethyl groups;

a lower alkoxycarbonyloxymethyl group in which the alkoxy group is as defined and exemplified above in relation to substituent α etc., such as the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl and pentyloxycarbonyloxymethyl groups; and a (2-oxo-1,3-dioxolen-4-yl)methyl group in which the 5-position of the dioxolene ring may be substituted with a lower alkyl group or an aryl group, as defined and exemplified above in relation to R and $R^4$, respectively, such as the (5-phenyl-2-oxo-1,3-dioxolen yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl and (5-butyl-2-oxo-1,3-dioxolen-4-yl)methyl groups.

Of these, we prefer the alkanoyl groups having from 1 to 12 carbon atoms, the alkoxycarbonyl groups having from 2 to 5 carbon atoms, the aralkyloxycarbonyl groups having 7 to 8 carbon atoms, the alkanoyloxymethyl groups having from 3 to 6 carbon atoms, the alkoxycarbonyloxymethyl groups having from 3 to 6 carbon atoms and the 5-substituted (2-oxo-1,3-dioxolen-4-yl)methyl group, more preferably the acetyl, propionyl, butyryl, isobutyryl, valeryl, isovaleryl, pivaloyl, methoxycarbonyl, ethoxycarbonyl, benzyloxycarbonyl, acetoxymethyl, propionyloxymethyl, methoxycarbonyloxymethyl, ethoxycarbonyloxymethyl, (5-methyl-2-oxo-1,3-dioxolen-4-yl)methyl and (5-phenyl-2-oxo-1,3-dioxolen-4-yl)methyl groups, and most preferably the acetyl group.

Specific examples of $R^1$ preferably include the methyl, ethyl, amino, acetylamino, propionylamino, butyrylamino, isobutyrylamino, valerylamino, isovalerylamino, pivaloylamino, methoxycarbonylamino, ethoxycarbonylamino, benzyloxycarbonyl amino, acetoxymethyl amino, propionyloxymethyl amino, methoxycarbonyloxymethylamino, ethoxycarbonyloxymethylamino, (5-methyl-2-oxo-1,3-dioxolen-4-yl)methylamino and (5-phenyl-2-oxo-1,3-dioxolen-4-yl)methylamino groups, more preferably the methyl, amino and acetylamino groups, and most preferably the amino and acetylamino groups.

Specific examples of $R^2$ preferably include:

the unsubstituted phenyl group;

phenyl groups having from 1 to 3 substituents selected from mercapto groups, $C_1$–$C_4$ alkanoylthio groups, halogen atoms, $C_1$–$C_4$ alkyl groups, $C_1$–$C_4$ alkoxy groups, $C_1$–$C_4$ alkylthio groups and $C_1$–$C_4$ alkylsulfinyl groups, such as the 4-mercaptophenyl, 4-acetylthiophenyl, 4-propionylthiophenyl, 4-fluorophenyl, 4-chlorophenyl, 4-bromophenyl, p-tolyl, 4-ethylphenyl, 4-methoxyphenyl, 4-ethoxyphenyl, 4-methylthiophenyl, 4-ethylthiophenyl, 4-methylsulfinylphenyl, 4-ethylsulfinylphenyl, 3,4-difluorophenyl, 2,4-difluorophenyl, 3,4-dichlorophenyl, 2,4-dichlorophenyl, 3,4-dimethylphenyl, 3,4-dimethoxyphenyl, 3-chloro-4-fluorophenyl, 3-chloro-4-methoxyphenyl, 3-fluoro-4-methoxyphenyl, 3-methyl-4-methoxyphenyl, 3,5-dichloro-4-methoxyphenyl and 4-methoxy-3,5-dimethylphenyl groups;

trifluoromethyl-, difluoromethoxy- or trifluoromethoxy-substituted phenyl groups, such as the 4-trifluoromethylphenyl, 4-difluoromethoxyphenyl and 4-trifluoromethoxyphenyl groups;

methylenedioxy- or ethylenedioxy-substituted phenyl group such as the 3,4-methylenedioxyphenyl and 3,4-ethylenedioxyphenyl groups.

In the case where $R^2$ is a substituted phenyl group, the number of substituents is preferably from 1 to 3, more preferably 1 or 2.

Specific examples of $R^3$ preferably include hydrogen atoms; halogen atoms, such as the fluorine, chlorine, bromine and iodine atoms; $C_1$–$C_4$ alkyl groups, such as the methyl, ethyl, propyl, isopropyl, butyl, isobutyl, sec-butyl and t-butyl groups; and $C_1$–$C_4$ haloalkyl groups, such as the fluoromethyl, chloromethyl, bromomethyl, iodomethyl, difluoromethyl, trifluoromethyl, 2-fluoroethyl, 3-fluoropropyl, 4-fluorobutyl, 2-chloroethyl and 3-chloropropyl groups, more preferably hydrogen atoms; halogen atoms, such as the fluorine, chlorine, bromine and iodine atoms; and the methyl, ethyl, fluoromethyl, difluoromethyl, 2-fluoroethyl and 2-chloroethyl groups.

Specific examples of $R^4$ preferably include hydrogen atoms; $C_1$–$C_6$ alkyl groups, such as the methyl, ethyl, propyl, isopropyl, butyl, isobutyl, sec-butyl, t-butyl, pentyl and hexyl groups; any of these alkyl groups having a substituent selected from hydroxy, halogen (such as fluorine, chlorine, bromine or iodine) and $C_1$–$C_4$ alkoxy (such as methoxy, ethoxy, propoxy, isopropoxy, butoxy, isobutoxy, sec-butoxy and t-butoxy); $C_3$–$C_7$ cycloalkyl groups, such as the cyclopropyl, cyclobutyl, cyclopentyl, cyclohexyl and cycloheptyl groups; $C_6$–$C_{10}$ aryl groups, such as the phenyl and naphthyl groups, which may be unsubstituted or may have one or more of the following substituents γ; $C_6$–$C_{10}$ aryl $C_1$–$C_4$ alkyl groups, such as the benzyl, phenethyl, 3-phenylpropyl, 4-phenylbutyl, 1-naphthylmethyl and 2-naphthylmethyl groups, which may be unsubstituted or may have one or more of the following substituents γ in the aryl moiety;

substituents γ include: halogen atoms, such as the fluorine, chlorine, bromine and iodine atoms; $C_1$–$C_4$ alkyl groups, such as the methyl, ethyl, propyl, isopropyl, butyl, isobutyl, sec-butyl and t-butyl groups; $C_1$–$C_4$ haloalkyl groups, such as the fluoromethyl, difluoromethyl, trifluoromethyl, chloromethyl, trichloromethyl, chlorodifluoromethyl, 2-fluoroethyl, 2-chloroethyl, 2-bromoethyl, 2-iodoethyl, 3-fluoropropyl and 4-fluoropropyl groups; $C_1$–$C_4$ alkoxy groups, such as the methoxy, ethoxy, propoxy, isopropoxy, butoxy, isobutoxy, sec-butoxy and t-butoxy groups; and $C_3$–$C_7$ cycloalkyloxy groups, such as the cyclopropyloxy, cyclobutyloxy, cyclopentyloxy, cyclohexyloxy and cycloheptyloxy groups.

Preferred examples of $R^4$ include: hydrogen atoms; $C_1$–$C_4$ alkyl groups, such as the methyl, ethyl, isopropyl, butyl and isobutyl groups; $C_1$–$C_4$ mono-, di- or trihaloalkyl groups, such as the fluoromethyl, difluoromethyl, chlorodifluoromethyl, bromodifluoromethyl, trifluoromethyl, 2-fluoroethyl and 2,2,2-trifluoroethyl groups, hydroxymethyl groups; $C_1$–$C_4$ alkoxymethyl groups, such as the methoxymethyl and ethoxymethyl groups; $C_3$–$C_6$ cycloalkyl groups, such as the cyclopropyl, cyclobutyl, cyclopentyl and cyclohexyl groups; phenyl groups; mono- or difluorophenyl groups, such as the 4-fluorophenyl and 2,4-difluorophenyl groups; mono- or dimethoxyphenyl groups, such as the 4-methoxyphenyl and 3,4-dimethoxyphenyl groups; tolyl groups, such as the p-tolyl and o-tolyl groups; cyclopentyloxy-(methoxy)phenyl groups, such as the 3-cyclopentyloxy-4-methoxyphenyl group; trifluoromethylphenyl groups, such as the 4-trifluoromethylphenyl group; benzyl groups; substituted benzyl groups, such as the 4-methoxybenzyl and 3-cyclopentyloxy-4-methoxybenzyl groups; phenethyl groups; naphthyl groups, such as the 1-naphthyl and 2-naphthyl groups; and naphthylmethyl groups, such as the 1-naphthylmethyl and 2-naphthylmethyl groups.

Certain of the compounds of the present invention, specifically the compounds of formula (I) and (II), possess an acidic group and can thus form salts with cations. The nature of the salt is not critical to the present invention, provided that it is pharmaceutically acceptable, that is that the salt is neither less active (or unacceptably less active) nor more toxic (or unacceptably more toxic) than the free acid. Such salts include, for example: salts with alkali metals, such as sodium, potassium or lithium; salts with alkaline earth metals, such as calcium or magnesium; salts with other metals, such as aluminum, iron, zinc, copper, nickel or cobalt; other inorganic salts, such as the ammonium salt; salts with organic amines, such as t-octylamine, dibenzylamine, morpholine, glucosamine, phenylglycine alkyl ester, ethylenediamine, N-methylglucamine, guanidine, diethylamine, triethylamine, dicyclohexylamine, N,N'-dibenzylethylenediamine, chloroprocaine, procaine, diethanolamine, N-benzyl-N-phenethylamine, piperazine, tetramethyl ammonium or tris(hydroxymethyl) aminomethane.

Further, when the compounds of formula (I) and (II) and salts thereof are allowed to stand in the atmosphere, they may adsorb moisture to form hydrates. Such hydrates are also included in the present invention.

Further, the compounds of formula (I) and (II) and salts thereof sometimes absorb certain kinds of solvents to afford solvates, and such solvates are also included in the present invention.

Certain of the compounds of formula (I) and (II) of the present invention may have asymmetric carbon atoms in their molecule, and stereoisomers in the R-configuration or the S-configuration would then exist. Each of these stereoisomers and mixtures thereof in any desired proportion are all included in the present invention.

Specific examples of the compounds of formula (I) and (II) employed in the method and composition of the present invention include, for example, those shown in the following Table 1 [compounds of formula (I)] and Table 2 [compounds of formula (II)].

In the Tables, the following abbreviations are used:

Ac acetyl;
Bu butyl;
Byr butyryl;
iByr isobutyryl;
Bz benzyl;
Et ethyl;
For formyl;
Me methyl;
Ph phenyl;
Piv pivaloyl;
cPn cyclopentyl;
Pr propyl;
cPr cyclopropyl;
iPr isopropyl;
Prn propionyl;
iVal isovaleryl; and
Val valeryl.

TABLE 1

| Cpd. No. | R | $R^1$ | $R^2$ | $R^3$ | $R^4$ |
|---|---|---|---|---|---|
| 1-1 | H | Me | Ph | H | H |
| 1-2 | H | Me | Ph | H | Me |
| 1-3 | H | Me | 4-F—Ph | H | H |
| 1-4 | H | Me | 4-F—Ph | F | H |
| 1-5 | H | Me | 4-F—Ph | Cl | H |
| 1-6 | H | Me | 4-F—Ph | Br | H |
| 1-7 | H | Me | 4-F—Ph | I | H |
| 1-8 | H | Me | 4-F—Ph | Me | H |
| 1-9 | H | Me | 4-F—Ph | Et | H |
| 1-10 | H | Me | 4-F—Ph | Pr | H |
| 1-11 | H | Me | 4-F—Ph | Bu | H |
| 1-12 | H | Me | 4-F—Ph | $CH_2F$ | H |
| 1-13 | H | Me | 4-F—Ph | $CHF_2$ | H |
| 1-14 | H | Me | 4-F—Ph | $CF_3$ | H |
| 1-15 | H | Me | 4-F—Ph | H | Me |
| 1-16 | H | Me | 4-F—Ph | F | Me |
| 1-17 | H | Me | 4-F—Ph | Cl | Me |
| 1-18 | H | Me | 4-F—Ph | Br | Me |
| 1-19 | H | Me | 4-F—Ph | I | Me |
| 1-20 | H | Me | 4-F—Ph | Me | Me |
| 1-21 | H | Me | 4-F—Ph | Et | Me |
| 1-22 | H | Me | 4-F—Ph | Pr | Me |
| 1-23 | H | Me | 4-F—Ph | H | Et |
| 1-24 | H | Me | 4-F—Ph | H | Pr |
| 1-25 | H | Me | 4-F—Ph | H | Bu |
| 1-26 | H | Me | 4-F—Ph | H | cPr |
| 1-27 | H | Me | 4-F—Ph | H | Ph |
| 1-28 | H | Me | 4-F—Ph | H | $CH_2Ph$ |
| 1-29 | H | Me | 4-F—Ph | H | $CHF_2$ |
| 1-30 | H | Me | 4-F—Ph | Me | $CHF_2$ |
| 1-31 | H | Me | 4-F—Ph | H | $CF_3$ |
| 1-32 | H | Me | 4-F—Ph | Me | $CF_3$ |
| 1-33 | H | Me | 4-MeO—Ph | H | H |
| 1-34 | H | Me | 4-MeO—Ph | H | Me |
| 1-35 | H | Me | 4-Cl—Ph | H | H |
| 1-36 | H | Me | 4-Cl—Ph | H | Me |
| 1-37 | H | Me | 4-Me—Ph | H | H |
| 1-38 | H | Me | 4-Me—Ph | H | Me |
| 1-39 | H | Me | 3-Cl-4-F—Ph | H | H |
| 1-40 | H | Me | 3-Cl-4-F—Ph | H | Me |
| 1-41 | H | Me | 3,4-methylenedioxy-Ph | H | H |
| 1-42 | H | Me | 3,4-methylenedioxy-Ph | H | Me |
| 1-43 | H | Me | 3-Cl-4-MeO—Ph | H | H |
| 1-44 | H | Me | 3-Cl-4-MeO—Ph | H | Me |
| 1-45 | H | Me | 4-$CF_3$—Ph | H | H |
| 1-46 | H | Me | 4-$CF_3$O—Ph | H | H |
| 1-47 | H | Me | 3-F-4-MeO—Ph | H | H |
| 1-48 | H | Me | 3-F-4-MeO—Ph | H | Me |
| 1-49 | H | Me | 3-Me-4-MeO—Ph | H | H |
| 1-50 | H | Me | 3-Me-4-MeO—Ph | H | Me |
| 1-51 | H | Me | 3,4-diF—Ph | H | H |
| 1-52 | H | Me | 3,4-diF—Ph | H | Me |
| 1-53 | H | Me | 2,4-diF—Ph | H | H |
| 1-54 | H | Me | 2,4-diF—Ph | H | Me |
| 1-55 | H | Me | 3,4-diMe—Ph | H | H |
| 1-56 | H | Me | 3,4-diMe—Ph | H | Me |
| 1-57 | H | Me | 3,4-diCl—Ph | H | H |
| 1-58 | H | Me | 3,4-diCl—Ph | H | Me |
| 1-59 | H | Me | 3,4-di(MeO)—Ph | H | H |
| 1-60 | H | Me | 3,4-di(MeO)—Ph | H | Me |

TABLE 1-continued

| Cpd. No. | R | R¹ | R² | R³ | R⁴ |
|---|---|---|---|---|---|
| 1-61 | H | Me | 4-F—Ph | H | CH$_2$OH |
| 1-62 | H | Me | 4-F—Ph | Me | CH$_2$OH |
| 1-63 | H | Me | 4-F—Ph | H | CH$_2$OMe |
| 1-64 | H | Me | 4-MeO—Ph | H | CM$_2$OH |
| 1-65 | H | Me | 4-MeO—Ph | H | CH$_2$OMe |
| 1-66 | H | Me | 4-Cl—Ph | H | CH$_2$OH |
| 1-67 | H | Me | 4-Cl—Ph | H | CH$_2$OMe |
| 1-68 | H | Me | 4-Me—Ph | H | CH$_2$OH |
| 1-69 | H | Me | 4-Me—Ph | H | CH$_2$OMe |
| 1-70 | H | NH$_2$ | Ph | H | H |
| 1-71 | H | NH$_2$ | Ph | H | Me |
| 1-72 | H | NH$_2$ | Ph | Me | H |
| 1-73 | H | NH$_2$ | 4-F—Ph | H | H |
| 1-74 | H | NH$_2$ | 4-F—Ph | H | Me |
| 1-75 | H | NH$_2$ | 4-F—Ph | Cl | Me |
| 1-76 | H | NH$_2$ | 4-F—Ph | Me | H |
| 1-77 | H | NH$_2$ | 4-F—Ph | H | Et |
| 1-78 | H | NH$_2$ | 4-F—Ph | H | Pr |
| 1-79 | H | NH$_2$ | 4-F—Ph | H | Bu |
| 1-80 | H | NH$_2$ | 4-F—Ph | H | cPr |
| 1-81 | H | NH$_2$ | 4-F—Ph | H | Ph |
| 1-82 | H | NH$_2$ | 4-F—Ph | H | CH$_2$Ph |
| 1-83 | H | NH$_2$ | 4-F—Ph | H | CHF$_2$ |
| 1-84 | H | NH$_2$ | 4-F—Ph | H | CF$_3$ |
| 1-85 | H | NH$_2$ | 4-MeO—Ph | H | H |
| 1-86 | H | NH$_2$ | 4-MeO—Ph | H | Me |
| 1-87 | H | NH$_2$ | 4-MeO—Ph | H | Bu |
| 1-88 | H | NH$_2$ | 4-MeO—Ph | Me | H |
| 1-89 | H | NH$_2$ | 4-EtO—Ph | H | H |
| 1-90 | H | NH$_2$ | 4-EtO—Ph | H | Me |
| 1-91 | H | NH$_2$ | 4-EtO—Ph | Me | H |
| 1-92 | H | NH$_2$ | 4-PrO—Ph | H | Me |
| 1-93 | H | NH$_2$ | 4-MeS—Ph | H | H |
| 1-94 | H | NH$_2$ | 4-MeS—Ph | H | Me |
| 1-95 | H | NH$_2$ | 4-MeS—Ph | Me | H |
| 1-96 | H | NH$_2$ | 4-Cl—Ph | H | H |
| 1-97 | H | NH$_2$ | 4-Cl—Ph | H | Me |
| 1-98 | H | NH$_2$ | 4-Cl—Ph | Me | H |
| 1-99 | H | NH$_2$ | 4-Me—Ph | H | H |
| 1-100 | H | NH$_2$ | 4-Me—Ph | H | Me |
| 1-101 | H | NH$_2$ | 4-Me—Ph | Me | H |
| 1-102 | H | NH$_2$ | 3-Cl-4-F—Ph | H | H |
| 1-103 | H | NH$_2$ | 3-Cl-4-F—Ph | H | Me |
| 1-104 | H | NH$_2$ | 3-Cl-4-F—Ph | Me | H |
| 1-105 | H | NH$_2$ | 3,4-methylenedioxy-Ph | H | H |
| 1-106 | H | NH$_2$ | 3,4-methylenedioxy-Ph | H | Me |
| 1-107 | H | NH$_2$ | 3-Cl-4-MeO—Ph | H | H |
| 1-108 | H | NH$_2$ | 3-Cl-4-MeO—Ph | H | Me |
| 1-109 | H | NH$_2$ | 3-Cl-4-MeO—Ph | Me | H |
| 1-110 | H | NH$_2$ | 4-CF$_3$—Ph | H | H |
| 1-111 | H | NH$_2$ | 4-CF$_3$O—Ph | H | H |
| 1-112 | H | NH$_2$ | 3-F-4-MeO—Ph | H | H |
| 1-113 | H | NH$_2$ | 3-F-4-MeO—Ph | H | Me |
| 1-114 | H | NH$_2$ | 3-F-4-MeO—Ph | Me | H |
| 1-115 | H | NH$_2$ | 3-Me-4-MeO—Ph | H | H |
| 1-116 | H | NH$_2$ | 3-Me-4-MeO—Ph | H | Me |
| 1-117 | H | NH$_2$ | 3-Me-4-MeO—Ph | Me | H |
| 1-118 | H | NH$_2$ | 3,4-diF—Ph | H | H |
| 1-119 | H | NH$_2$ | 3,4-diF—Ph | H | Me |
| 1-120 | H | NH$_2$ | 3,4-diF—Ph | Me | H |
| 1-121 | H | NH$_2$ | 2,4-diF—Ph | H | H |
| 1-122 | H | NH$_2$ | 2,4-diF—Ph | H | Me |
| 1-123 | H | NH$_2$ | 2,4-diF—Ph | Me | H |
| 1-124 | H | NH$_2$ | 3,4-diMe—Ph | H | H |
| 1-125 | H | NH$_2$ | 3,4-diMe—Ph | H | Me |
| 1-126 | H | NH$_2$ | 3,4-diMe—Ph | Me | H |
| 1-127 | H | NH$_2$ | 2,4-diCl—Ph | H | H |
| 1-128 | H | NH$_2$ | 2,4-diCl—Ph | H | Me |
| 1-129 | H | NH$_2$ | 2,4-diCl—Ph | Me | H |
| 1-130 | H | NH$_2$ | 3,4-diCl—Ph | H | H |
| 1-131 | H | NH$_2$ | 3,4-diCl—Ph | H | Me |
| 1-132 | H | NH$_2$ | 3,4-diCl—Ph | Me | H |
| 1-133 | H | NH$_2$ | 3,4-di(MeO)—Ph | H | H |
| 1-134 | H | NH$_2$ | 3,4-di(MeO)—Ph | H | Me |
| 1-135 | H | NH$_2$ | 4-F—Ph | H | CH$_2$OH |
| 1-136 | H | NH$_2$ | 4-F—Ph | H | CH$_2$OMe |
| 1-137 | H | NH$_2$ | 4-MeO—Ph | H | CH$_2$OH |

TABLE 1-continued

| Cpd. No. | R | R¹ | R² | R³ | R⁴ |
|---|---|---|---|---|---|
| 1-138 | H | NH₂ | 4-MeO—Ph | H | CH₂OMe |
| 1-139 | H | NH₂ | 4-Cl—Ph | H | CH₂OH |
| 1-140 | H | NH₂ | 4-Cl—Ph | H | CH₂OMe |
| 1-141 | H | NH₂ | 4-Me—Ph | H | CH₂OH |
| 1-142 | H | NH₂ | 4-Me—Ph | H | CH₂OMe |
| 1-143 | H | NH₂ | 4-Et—Ph | H | H |
| 1-144 | H | NH₂ | 4-Et—Ph | H | Me |
| 1-145 | H | NH₂ | 4-Et—Ph | Me | H |
| 1-146 | H | NH₂ | 2,4,6-triMe—Ph | H | Me |
| 1-147 | H | NH₂ | 4-MeO—Ph | Cl | H |
| 1-148 | H | NH₂ | 4-MeO—Ph | Br | H |
| 1-149 | H | NH₂ | 4-MeO—Ph | Cl | Me |
| 1-150 | H | NH₂ | 2-F-4-Cl—Ph | H | Me |
| 1-151 | H | NH₂ | 4-EtO—Ph | Cl | H |
| 1-152 | H | NH₂ | 4-MeS—Ph | Cl | H |
| 1-153 | H | NH₂ | 4-MeSO—Ph | H | Me |
| 1-154 | H | NH₂ | 4-EtS—Ph | H | Me |
| 1-155 | H | NH₂ | 2,4-diCl—Ph | Cl | H |
| 1-156 | H | NH₂ | 4-SH—Ph | H | Me |
| 1-157 | H | NH₂ | 4-AcS—Ph | H | Me |
| 1-158 | 3-F | NH₂ | 4-MeO—Ph | H | Me |
| 1-159 | 3-F | NH₂ | 4-EtO—Ph | H | Me |
| 1-160 | 3-F | NH₂ | 3,4-diMe—Ph | H | Me |
| 1-161 | 3-F | NH₂ | 4-Cl—Ph | H | Me |
| 1-162 | 3-F | NH₂ | 4-F—Ph | H | Me |
| 1-163 | 3-F | NH₂ | 4-SH—Ph | H | Me |
| 1-164 | 3-F | NH₂ | 4-MeS—Ph | H | Me |
| 1-165 | 3-F | NH₂ | 4-EtS—Ph | H | Me |
| 1-166 | 3-F | NH₂ | 4-AcS—Ph | H | Me |
| 1-167 | 3-Me | NH₂ | 4-MeO—Ph | H | Me |
| 1-168 | 3-Me | NH₂ | 4-EtO—Ph | H | Me |
| 1-169 | 3-Me | NH₂ | 3,4-diMe—Ph | H | Me |
| 1-170 | 3-Me | NH₂ | 4-Cl—Ph | H | Me |
| 1-171 | 3-Me | NH₂ | 4-F—Ph | H | Me |
| 1-172 | 3-Me | NH₂ | 4-MeS—Ph | H | Me |
| 1-173 | H | NHFor | 4-MeS—Ph | H | Me |
| 1-174 | H | NHAc | 4-MeS—Ph | H | Me |
| 1-175 | H | NHPrn | 4-MeS—Ph | H | Me |
| 1-176 | H | NHByr | 4-MeS—Ph | H | Me |
| 1-177 | H | NHiByr | 4-MeS—Ph | H | Me |
| 1-178 | H | NHVal | 4-MeS—Ph | H | Me |
| 1-179 | H | NHiVal | 4-MeS—Ph | H | Me |
| 1-180 | H | NHPiv | 4-MeS—Ph | H | Me |
| 1-181 | H | NH(MeOCO) | 4-MeS—Ph | H | Me |
| 1-182 | H | NH(EtOCO) | 4-MeS—Ph | H | Me |
| 1-183 | H | NH(BzOCO) | 4-MeS—Ph | H | Me |
| 1-184 | H | NH(AcOCH₂) | 4-MeS—Ph | H | Me |
| 1-185 | H | NH(PrnOCH₂) | 4-MeS—Ph | H | Me |
| 1-186 | H | NH(MeOCOOCH₂) | 4-MeS—Ph | H | Me |
| 1-187 | H | NH(EtOCOOCH₂) | 4-MeS—Ph | H | Me |
| 1-188 | H | NH[(5-Me-2-oxo-1,3-dioxolen-4-yl)CH₂] | 4-MeS—Ph | H | Me |
| 1-189 | H | NH[(5-Ph-2-oxo-1,3-dioxolen-4-yl)CH₂] | 4-MeS—Ph | H | Me |

TABLE 2

| Cpd. No. | R | R¹ | R² | R³ | R⁴ |
|---|---|---|---|---|---|
| 2-1 | H | Me | Ph | H | H |
| 2-2 | H | Me | Ph | H | Me |
| 2-3 | H | Me | 4-F—Ph | H | H |
| 2-4 | H | Me | 4-F—Ph | F | H |
| 2-5 | H | Me | 4-F—Ph | Cl | H |
| 2-6 | H | Me | 4-F—Ph | Br | H |
| 2-7 | H | Me | 4-F—Ph | I | H |
| 2-8 | H | Me | 4-F—Ph | Me | H |
| 2-9 | H | Me | 4-F—Ph | Et | H |
| 2-10 | H | Me | 4-F—Ph | Pr | H |
| 2-11 | H | Me | 4-F—Ph | H | Me |
| 2-12 | H | Me | 4-F—Ph | H | Et |
| 2-13 | H | Me | 4-F—Ph | H | Pr |
| 2-14 | H | Me | 4-F—Ph | H | Bu |
| 2-15 | H | Me | 4-F—Ph | H | cPr |

TABLE 2-continued

| Cpd. No. | R | R¹ | R² | R³ | R⁴ |
|---|---|---|---|---|---|
| 2-16 | H | Me | 4-F—Ph | H | Ph |
| 2-17 | H | Me | 4-F—Ph | H | CH$_2$Ph |
| 2-18 | H | Me | 4-F—Ph | H | CHF$_2$ |
| 2-19 | H | Me | 4-F—Ph | H | CF$_3$ |
| 2-20 | H | Me | 4-MeO—Ph | H | H |
| 2-21 | H | Me | 4-MeO—Ph | Me | H |
| 2-22 | H | Me | 4-MeO—Ph | H | Me |
| 2-23 | H | Me | 4-Cl—Ph | H | H |
| 2-24 | H | Me | 4-Cl—Ph | Me | H |
| 2-25 | H | Me | 4-Me—Ph | H | H |
| 2-26 | H | Me | 4-Me—Ph | Me | H |
| 2-27 | H | Me | 4-Me—Ph | H | Me |
| 2-28 | H | Me | 3-Cl-4-F—Ph | H | H |
| 2-29 | H | Me | 3-Cl-4-F—Ph | H | Me |
| 2-30 | H | Me | 3,4-Methylenedioxy-Ph | H | H |
| 2-31 | H | Me | 3,4-Methylenedioxy-Ph | H | Me |
| 2-32 | H | Me | 3-Cl-4-MeO—Ph | H | H |
| 2-33 | H | Me | 3-Cl-4-MeO—Ph | H | Me |
| 2-34 | H | Me | 4-CF$_3$—Ph | H | H |
| 2-35 | H | Me | 4-CF$_3$O—Ph | H | H |
| 2-36 | H | Me | 4-CHF$_2$O—Ph | H | H |
| 2-37 | H | Me | 4-CHF$_2$O—Ph | Me | H |
| 2-38 | H | Me | 3-F-4-MeO—Ph | H | H |
| 2-39 | H | Me | 3-F-4-MeO—Ph | H | Me |
| 2-40 | H | Me | 3-Me-4-MeO—Ph | H | H |
| 2-41 | H | Me | 3-Me-4-MeO—Ph | H | Me |
| 2-42 | H | Me | 3,4-diF—Ph | H | H |
| 2-43 | H | Me | 3,4-diF—Ph | H | Me |
| 2-44 | H | Me | 2,4-diF—Ph | H | H |
| 2-45 | H | Me | 2,4-diF—Ph | H | Me |
| 2-46 | H | Me | 3,4-diMe—Ph | H | H |
| 2-47 | H | Me | 3,4-diCl—Ph | H | H |
| 2-48 | H | Me | 3,4-diCl—Ph | H | Me |
| 2-49 | H | Me | 3,4-di(MeO)—Ph | H | H |
| 2-50 | H | Me | 3,4-di(MeO)—Ph | H | Me |
| 2-51 | H | Me | 4-F—Ph | H | CH$_2$OH |
| 2-52 | H | Me | 4-F—Ph | H | CH$_2$OMe |
| 2-53 | H | Me | 4-MeO—Ph | H | CH$_2$OH |
| 2-54 | H | Me | 4-MeO—Ph | H | CH$_2$OMe |
| 2-55 | H | Me | 4-Cl—Ph | H | CH$_2$OH |
| 2-56 | H | Me | 4-Cl—Ph | H | CH$_2$OMe |
| 2-57 | H | Me | 4-Me—Ph | H | CH$_2$OH |
| 2-58 | H | Me | 4-Me—Ph | H | CH$_2$OMe |
| 2-59 | H | NH$_2$ | Ph | H | H |
| 2-60 | H | NH$_2$ | Ph | H | Me |
| 2-61 | H | NH$_2$ | Ph | Me | H |
| 2-62 | H | NH$_2$ | 4-F—Ph | H | H |
| 2-63 | H | NH$_2$ | 4-F—Ph | H | Me |
| 2-64 | H | NH$_2$ | 4-F—Ph | Me | H |
| 2-65 | H | NH$_2$ | 4-F—Ph | H | Et |
| 2-66 | H | NH$_2$ | 4-F—Ph | H | Pr |
| 2-67 | H | NH$_2$ | 4-F—Ph | H | Bu |
| 2-68 | H | NH$_2$ | 4-F—Ph | H | cPr |
| 2-69 | H | NH$_2$ | 4-F—Ph | H | Ph |
| 2-70 | H | NH$_2$ | 4-F—Ph | H | CH$_2$Ph |
| 2-71 | H | NH$_2$ | 4-F—Ph | H | CHF$_2$ |
| 2-72 | H | NH$_2$ | 4-F—Ph | H | CF$_3$ |
| 2-73 | H | NH$_2$ | 4-MeO—Ph | H | H |
| 2-74 | H | NH$_2$ | 4-MeO—Ph | H | Me |
| 2-75 | H | NH$_2$ | 4-MeO—Ph | H | Et |
| 2-76 | H | NH$_2$ | 4-MeO—Ph | Me | H |
| 2-77 | H | NH$_2$ | 4-EtO—Ph | H | H |
| 2-78 | H | NH$_2$ | 4-EtO—Ph | H | Me |
| 2-79 | H | NH$_2$ | 4-EtO—Ph | Me | H |
| 2-80 | H | NH$_2$ | 4-PrO—Ph | H | Me |
| 2-81 | H | NH$_2$ | 4-MeS—Ph | H | H |
| 2-82 | H | NH$_2$ | 4-MeS—Ph | H | Me |
| 2-83 | H | NH$_2$ | 4-MeS—Ph | Me | H |
| 2-84 | H | NH$_2$ | 4-Cl—Ph | H | H |
| 2-85 | H | NH$_2$ | 4-Cl—Ph | H | Me |
| 2-86 | H | NH$_2$ | 4-Cl—Ph | Me | H |
| 2-87 | H | NH$_2$ | 4-Me—Ph | H | H |
| 2-88 | H | NH$_2$ | 4-Me—Ph | Me | H |
| 2-89 | H | NH$_2$ | 4-Me—Ph | H | Me |
| 2-90 | H | NH$_2$ | 4-Et—Ph | H | H |
| 2-91 | H | NH$_2$ | 4-Et—Ph | H | Me |
| 2-92 | H | NH$_2$ | 4-Et—Ph | Me | H |

TABLE 2-continued

| Cpd. No. | R | R¹ | R² | R³ | R⁴ |
|---|---|---|---|---|---|
| 2-93 | H | NH₂ | 4-iPr—Ph | H | Me |
| 2-94 | H | NH₂ | 3-Cl-4-F—Ph | H | H |
| 2-95 | H | NH₂ | 3-Cl-4-F—Ph | H | Me |
| 2-96 | H | NH₂ | 3-Cl-4-F—Ph | Me | H |
| 2-97 | H | NH₂ | 3,4-Methylenedioxy-Ph | H | H |
| 2-98 | H | NH₂ | 3,4-Methylenedioxy-Ph | H | Me |
| 2-99 | H | NH₂ | 3-Cl-4-MeO—Ph | H | H |
| 2-100 | H | NH₂ | 3-Cl-4-MeO—Ph | H | Me |
| 2-101 | H | NH₂ | 3-Cl-4-MeO—Ph | Me | H |
| 2-102 | H | NH₂ | 4-CF₃—Ph | H | Me |
| 2-103 | H | NH₂ | 4-CHF₂O—Ph | H | Me |
| 2-104 | H | NH₂ | 4-CF₃O—Ph | H | Me |
| 2-105 | H | NH₂ | 2-F-4-MeO—Ph | H | Me |
| 2-106 | H | NH₂ | 3-F-4-MeO—Ph | H | Me |
| 2-107 | H | NH₂ | 3-F-4-MeO—Ph | Me | H |
| 2-108 | H | NH₂ | 3-Me-4-MeO—Ph | H | H |
| 2-109 | H | NH₂ | 3-Me-4-MeO—Ph | H | Me |
| 2-110 | H | NH₂ | 3-Me-4-MeO—Ph | Me | H |
| 2-111 | H | NH₂ | 3,4-diF—Ph | H | H |
| 2-112 | H | NH₂ | 3,4-diF—Ph | H | Me |
| 2-113 | H | NH₂ | 3,4-diF—Ph | Me | H |
| 2-114 | H | NH₂ | 2,4-diF—Ph | H | H |
| 2-115 | H | NH₂ | 2,4-diF—Ph | H | Me |
| 2-116 | H | NH₂ | 2,4-diF—Ph | Me | H |
| 2-117 | H | NH₂ | 3,4-diMe—Ph | H | H |
| 2-118 | H | NH₂ | 3,4-diMe—Ph | H | Me |
| 2-119 | H | NH₂ | 3,4-diMe—Ph | Me | H |
| 2-120 | H | NH₂ | 2,4-diCl—Ph | H | H |
| 2-121 | H | NH₂ | 2,4-diCl—Ph | H | Me |
| 2-122 | H | NH₂ | 2,4-diCl—Ph | Me | H |
| 2-123 | H | NH₂ | 3,4-diCl—Ph | H | H |
| 2-124 | H | NH₂ | 3,4-diCl—Ph | H | Me |
| 2-125 | H | NH₂ | 3,4-diCl—Ph | Me | H |
| 2-126 | H | NH₂ | 3,4-di(MeO)—Ph | H | H |
| 2-127 | H | NH₂ | 3,4-di(MeO)—Ph | H | Me |
| 2-128 | H | NH₂ | 4-F—Ph | H | CH₂OH |
| 2-129 | H | NH₂ | 4-F—Ph | H | CH₂OMe |
| 2-130 | H | NH₂ | 4-MeO—Ph | H | CH₂OH |
| 2-131 | H | NH₂ | 4-MeO—Ph | H | CH₂OMe |
| 2-132 | H | NH₂ | 4-Cl—Ph | H | CH₂OH |
| 2-133 | H | NH₂ | 4-Cl—Ph | H | CH₂OMe |
| 2-134 | H | NH₂ | 4-Me—Ph | H | CH₂OH |
| 2-135 | H | NH₂ | 4-Me—Ph | H | CH₂OMe |
| 2-136 | H | NH₂ | 3,5-diCl-4-MeO—Ph | H | Me |
| 2-137 | H | NH₂ | 3,5-diMe-4-MeO—Ph | H | Me |
| 2-138 | H | NH₂ | 2,3-diCl—Ph | H | Me |
| 2-139 | H | NH₂ | 3,5-diCl—Ph | H | Me |
| 2-140 | H | NH₂ | 2,4,5-triMe—Ph | H | Me |
| 2-141 | H | NH₂ | 3-cPnO-4-MeO—Ph | H | Me |
| 2-142 | H | NH₂ | 3-CF₃-4-Cl—Ph | H | Me |
| 2-143 | H | NH₂ | 3-F-4-Me—Ph | H | Me |
| 2-144 | H | NH₂ | 3-Me-4-Cl—Ph | H | Me |
| 2-145 | H | NH₂ | 2,4-diMe—Ph | H | Me |
| 2-146 | H | NH₂ | 4-OH—Ph | H | Me |
| 2-147 | H | NH₂ | 3,5-diMe—Ph | H | Me |
| 2-148 | H | NHAc | 4-MeO—Ph | H | Me |
| 2-149 | H | NHAc | 3,4-diMe—Ph | H | Me |
| 2-150 | H | NH₂ | 4-MeO—Ph | H | 3-cPnO-4-MeO—Bz |
| 2-151 | H | NH₂ | 4-MeSO—Ph | H | Me |
| 2-152 | 3-F | NH₂ | 4-MeO—Ph | H | Me |
| 2-153 | 3-F | NH₂ | 4-EtO—Ph | H | Me |
| 2-154 | 3-F | NH₂ | 3,4-diMe—Ph | H | Me |
| 2-155 | 3-F | NH₂ | 4-Cl—Ph | H | Me |
| 2-156 | 3-F | NH₂ | 4-F—Ph | H | Me |
| 2-157 | 3-F | NH₂ | 4-SH—Ph | H | Me |
| 2-158 | 3-F | NH₂ | 4-MeS—Ph | H | Me |
| 2-159 | 3-F | NH₂ | 4-EtS—Ph | H | Me |
| 2-160 | 3-F | NH₂ | 4-AcS—Ph | H | Me |
| 2-161 | 3-Me | NH₂ | 4-MeO—Ph | H | Me |
| 2-162 | 3-Me | NH₂ | 4-EtO—Ph | H | Me |
| 2-163 | 3-Me | NH₂ | 3,4-diMe—Ph | H | Me |
| 2-164 | 3-Me | NH₂ | 4-MeS—Ph | H | Me |
| 2-165 | H | NHFor | 4-MeO—Ph | H | Me |
| 2-166 | H | NHPrn | 4-MeO—Ph | H | Me |
| 2-167 | H | NHByr | 4-MeO—Ph | H | Me |
| 2-168 | H | NHiByr | 4-MeO—Ph | H | Me |

TABLE 2-continued

| Cpd. No. | R | R¹ | R² | R³ | R⁴ |
|---|---|---|---|---|---|
| 2-169 | H | NHVal | 4-MeO—Ph | H | Me |
| 2-170 | H | NHiVal | 4-MeO—Ph | H | Me |
| 2-171 | H | NHPiv | 4-MeO—Ph | H | Me |
| 2-172 | H | NH(MeOCO) | 4-MeO—Ph | H | Me |
| 2-173 | H | NH(EtOCO) | 4-MeO—Ph | H | Me |
| 2-174 | H | NH(BzOCO) | 4-MeO—Ph | H | Me |
| 2-175 | H | NH(AcOCH₂) | 4-MeO—Ph | H | Me |
| 2-176 | H | NH(PrnOCH₂) | 4-MeO—Ph | H | Me |
| 2-177 | H | NH(MeOCOOCH₂) | 4-MeO—Ph | H | Me |
| 2-178 | H | NH(EtOCOOCH₂) | 4-MeO—Ph | H | Me |
| 2-179 | H | NH[(5-Me-2-oxo-1,3-dioxolen-4-yl)CH₂] | 4-MeO—Ph | H | Me |
| 2-180 | H | NH[(5-Ph-2-oxo-1,3-dioxolen-4-yl)CH₂] | 4-MeO—Ph | H | Me |
| 2-181 | H | NHFor | 4-EtO—Ph | H | Me |
| 2-182 | H | NHAc | 4-EtO—Ph | H | Me |
| 2-183 | H | NHPrn | 4-EtO—Ph | H | Me |
| 2-184 | H | NHByr | 4-EtO—Ph | H | Me |
| 2-185 | H | NHiByr | 4-EtO—Ph | H | Me |
| 2-186 | H | NHVal | 4-EtO—Ph | H | Me |
| 2-187 | H | NHiVal | 4-EtO—Ph | H | Me |
| 2-188 | H | NHPiv | 4-EtO—Ph | H | Me |
| 2-189 | H | NH(MeOCO) | 4-EtO—Ph | H | Me |
| 2-190 | H | NH(EtOCO) | 4-EtO—Ph | H | Me |
| 2-191 | H | NH(BzOCO) | 4-EtO—Ph | H | Me |
| 2-192 | H | NH(AcOCH₂) | 4-EtO—Ph | H | Me |
| 2-193 | H | NH(PrnOCH₂) | 4-EtO—Ph | H | Me |
| 2-194 | H | NH(MeOCOOCH₂) | 4-EtO—Ph | H | Me |
| 2-195 | H | NH(EtOCOOCH₂) | 4-EtO—Ph | H | Me |
| 2-196 | H | NH[(5-Me-2-oxo-1,3-dioxolen-4-yl)CH₂] | 4-EtO—Ph | H | Me |
| 2-197 | H | NH[(5-Ph-2-oxo-1,3-dioxolen-4-yl)CH₂] | 4-EtO—Ph | H | Me |
| 2-198 | H | NHFor | 3,4-diMe—Ph | H | Me |
| 2-199 | H | NHPrn | 3,4-diMe—Ph | H | Me |
| 2-200 | H | NHByr | 3,4-diMe—Ph | H | Me |
| 2-201 | H | NHiByr | 3,4-diMe—Ph | H | Me |
| 2-202 | H | NHVal | 3,4-diMe—Ph | H | Me |
| 2-203 | H | NHiVal | 3,4-diMe—Ph | H | Me |
| 2-204 | H | NHPiv | 3,4-diMe—Ph | H | Me |
| 2-205 | H | NH(MeOCO) | 3,4-diMe—Ph | H | Me |
| 2-206 | H | NH(EtOCO) | 3,4-diMe—Ph | H | Me |
| 2-207 | H | NH(BzOCO) | 3,4-diMe—Ph | H | Me |
| 2-208 | H | NH(AcOCH₂) | 3,4-diMe—Ph | H | Me |
| 2-209 | H | NH(PrnOCH₂) | 3,4-diMe—Ph | H | Me |
| 2-210 | H | NH(MeOCOOCH₂) | 3,4-diMe—Ph | H | Me |
| 2-211 | H | NH(EtOCOOCH₂) | 3,4-diMe—Ph | H | Me |
| 2-212 | H | NH[(5-Me-2-oxo-1,3-dioxolen-4-yl)CH₂] | 3,4-diMe—Ph | H | Me |
| 2-213 | H | NH[(5-Ph-2-oxo-1,3-dioxolen-4-yl)CH₂] | 3,4-diMe—Ph | H | Me |

Of the compounds listed above, preferred compounds are:
1) 3-methyl-2-(4-methylphenyl)-1-(4-sulfamoylphenyl)pyrrole,
2) 4-methyl-2-(4-methylphenyl)-1-(4-sulfamoylphenyl)pyrrole,
3) 1-(4-fluorophenyl)-2-(4-sulfamoylphenyl)pyrrole,
4) 1-(4-fluorophenyl)-4-methyl-2-(4-sulfamoylphenyl)pyrrole,
5) 5-fluoro-1-(4-fluorophenyl)-2-(4-methylsulfonylphenyl)pyrrole,
6) 2-(4-methoxyphenyl)-4-methyl-1-(4-sulfamoylphenyl)pyrrole,
7) 1-(4-methoxyphenyl)-4-methyl-2-(4-sulfamoylphenyl)pyrrole,
8) 4-ethyl-2-(4-methoxyphenyl)-1-(4-sulfamoylphenyl)pyrrole,
9) 2-(4-chlorophenyl)-4-methyl-1-(4-sulfamoylphenyl)pyrrole,
10) 4-methyl-2-(4-methylthiophenyl)-1-(4-sulfamoylphenyl)pyrrole,
11) 2-(4-ethoxyphenyl)-4-methyl-1-(4-sulfamoylphenyl)pyrrole,
12) 2-(4-methoxy-3-methylphenyl)-4-methyl-1-(4-sulfamoylphenyl)pyrrole,
13) 2-(3-fluoro-4-methoxyphenyl)-4-methyl-1-(4-sulfamoylphenyl)pyrrole,
14) 4-methyl-2-phenyl-1-(4-sulfamoylphenyl)pyrrole,
15) 2-(3,4-dimethylphenyl)-4-methyl-1-(4-sulfamoylphenyl)pyrrole,
16) 2-(3-chloro-4-methoxyphenyl)-4-methyl-1-(4-sulfamoylphenyl)pyrrole,
17) 4-methyl-1-(4-methylthiophenyl)-2-(4-sulfamoylphenyl)pyrrole,
18) 5-chloro-1-(4-methoxyphenyl)-2-(4-sulfamoylphenyl)pyrrole,
19) 1-(3,4-dimethylphenyl)-4-methyl-2-(4-sulfamoylphenyl)pyrrole,
20) 5-chloro-1-(4-ethoxyphenyl)-2-(4-sulfamoylphenyl)pyrrole,
21) 5-chloro-1-(4-methylthiophenyl)-2-(4-sulfamoylphenyl)pyrrole, 22)]-(4-ethylthiophenyl)-4-methyl-2-(4-sulfamoylphenyl) pyrrole,
23) 2-(3,5-dimethylphenyl)-4-methyl-1-(4-sulfamoylphenyl)pyrrole,
24) 1-(4-mercaptophenyl)-4-methyl-2-(4-sulfamoylphenyl) pyrrole,
25) 1-(4-acetylthiophenyl)-4-methyl-2-(4-sulfamoylphenyl) pyrrole,
26) 1-(4-acetylaminosulfonylphenyl)-4-methyl-2-(4-methoxyphenyl)pyrrole, and
27) 1-(4-acetylaminosulfonylphenyl)-4-methyl-2-(3,4-dimethylphenyl)pyrrole.

Of these, more preferred compounds are:
2) 4-methyl-2-(4-methylphenyl)-1-(4-sulfamoylphenyl) pyrrole,
6) 2-(4-methoxyphenyl)-4-methyl-1-(4-sulfamoylphenyl) pyrrole,
9) 2-(4-chlorophenyl)-4-methyl-1-(4-sulfamoylphenyl) pyrrole,
10) 4-methyl-2-(4-methylthiophenyl)-1-(4-sulfamoylphenyl)pyrrole,
11) 2-(4-ethoxyphenyl)-4-methyl-1-(4-sulfamoylphenyl) pyrrole,
12) 2-(4-methoxy-3-methylphenyl)-4-methyl-1-(4-sulfamoylphenyl)pyrrole,
13) 2-(3-fluoro-4-methoxyphenyl)-4-methyl-1-(4-sulfamoylphenyl)pyrrole,
15) 2-(3,4-dimethylphenyl)-4-methyl-1-(4-sulfamoylphenyl)pyrrole,
17) 4-methyl-1-(4-methylthiophenyl)-2-(4-sulfamoylphenyl)pyrrole,
26) 1-(4-acetylaminosulfonylphenyl)-4-methyl-2-(4-methoxyphenyl)pyrrole, and
27) 1-(4-acetylaminosulfonylphenyl)-4-methyl-2-(3,4-dimethylphenyl)pyrrole.

Of these, the most preferred compounds are:
11) 2-(4-ethoxyphenyl)-4-methyl-1-(4-sulfamoylphenyl) pyrrole,
15) 2-(3,4-dimethylphenyl)-4-methyl-1-(4-sulfamoylphenyl)pyrrole,
17) 4-methyl-1-(4-methylthiophenyl)-2-(4-sulfamoylphenyl)pyrrole,
26) 1-(4-acetylaminosulfonylphenyl)-4-methyl-2-(4-methoxyphenyl)pyrrole, and
27) 1-(4-acetylaminosulfonylphenyl)-4-methyl-2-(3,4-dimethylphenyl)pyrrole.

The compounds of formula (I), compounds of formula (II) and pharmaceutically acceptable salts of these compounds are known compounds and a method of preparing these compounds is disclosed in European Patent Publication EP-799823A, the disclosure of which is incorporated herein by reference.

The chemical names of the compounds of formulae (III) to (XIV), respectively, are:
(III): 3-(3,4-difluorophenyl)-4-(4-methanesulfonylphenyl)-5H-furan-2-one,
(IV): 4-(5-p-tolyl-3-trifluoromethyl-1'-pyrazol-1-yl) benzenesulfonamide,
(V): N-[6-(2,4-difluorophenylthio)-1-oxoindan-5-yl] methanesulfonamide,
(VI): 4-hydroxy-2-methyl-N-(5-methylthiazol-2-yl)-2H-1,2-benzothiazine-3-carboxamide-1,1-dioxide,
(VII): N-(4-Nitro-2-phenoxyphenyl)methanesulfonamide,
(VIII): 4-(4-cyclohexyl-2-methyloxazol-5-yl)-2-fluorobenzenesulfonamide,
(IX): N-(3-formylamino-4-oxo-6-phenoxy-4H-1-benzopyran-7-yl)methanesulfonamide,
(X): (E)-2-ethyl-5-(3,5-di-t-butyl-4-hydroxy)benzylidene-1,2-isothiazolidine-1,1-dioxide,
(XI): 1-(4-methanesulfonylphenyl)-2-(4-fluorophenyl) cyclopentene,
(XII): 3-phenyl-4-(4-methanesulfonylphenyl)-5H-furan-2-one, and
(XIII): 2-(3,5-difluorophenyl)-3-(4-methanesulfonylphenyl)-2-cyclopenten-1-one.
(XIV): 4-[5-methyl-3-phenylisoxazol-4-yl] benzenesulfonamide.

These compounds are disclosed in International publication number WO95/00501, J. Med. Chem., 40, 1347 (1997), International publication number WO94/13635, Pharmacology, 55, 44 (1997), Prostaglandins, 47, 55 (1994), Japanese publication number Hei 9-52882, Jpn. J. Pharmacol., 67, 305 (1995), Inflamm. Res., 47, Suppl. 3, S257 (1997), J. Med. Chem., 38, 4570 (1995), EP 863 134, U.S. Pat. No. 5,474,995 or WO 98/06708, the disclosures of which are incorporated herein by reference.

Since the compounds of the present invention have excellent activity for the prevention or inhibition of cachexia and very little toxicity, they are useful as preventive and therapeutic agents for cachexia They are also useful for the treatment of tumor-related disorders, and can be used to inhibit the growth and/or metastasis of tumors.

Moreover, if desired, one or more of the compounds of the present invention [i.e. the compounds of formulae (I) to (XIV), inclusive] may be used in association with one or more other agents for the prevention or inhibition for tumor growth, and the compounds of the present invention and other agents may be administered simultaneously, separately or sequentially.

The other antitumor agent is preferably selected from a group consisting of 5-fluorouracil, cisplatin, tamoxifen, paclitaxel, docetaxel and irinotecan. Especially in the case of simultaneous administration, the compound of formula (I) or (II) or a pharmaceutically acceptable salt thereof and the other antitumor agent may be contained in a single composition.

The composition of the present invention may be in any conventional form, depending on the route of administration. For example, for oral administration, it may be in the form of tablets, capsules, granules, powders or syrups. For non-oral administration it may be in the form of injections or suppositories. These formulations are prepared according to known methods and may include additives such as are well known in the art, for example excipients (e.g., organic excipients including sugar derivatives, such as lactose, sucrose, glucose, mannitol and sorbitol; starch derivatives, such as corn starch, potato starch, α-starch and dextrin; cellulose derivatives, such as crystalline cellulose; gum arabic; dextran; and Pullulan, inorganic excipients including silicate derivatives, such as light silicic acid anhydride, synthetic aluminum silicate, calcium silicate and magnesium metasilicate aluminate; phosphates, such as calcium hydrogenphosphate; carbonates, such as calcium carbonate; and sulfates, such as calcium sulfate), lubricants (e.g., stearic acid and metal salts thereof, including stearic acid, calcium stearate and magnesium stearate; talc; colloidal silica; waxes, such as beeswax and spermaceti; boric acid; adipic acid; sulfates, such as sodium sulfate; glycol; fumaric acid; sodium benzoate; DL-leucine; fatty acid sodium salts; lauryl sulfates, such as sodium lauryl sulfate and magnesium lauryl sulfate; silicic acids, such as silicic acid anhydride and silicic acid hydrate; and the above-mentioned starch derivatives), binders (e.g., hydroxypropyl cellulose, hydroxypropylmethyl cellulose, polyvinyl pyrrolidone, Macrogol and similar compounds to the above-mentioned excipients), disintegrating agents (e.g., cellulose derivatives, such as low-substituted hydroxypropyl cellulose, carboxymethyl cellulose, calcium carboxymethyl cellulose, internally bridged sodium carboxymethyl cellulose; chemically modified starch-celluloses, such as carboxymethyl starch, sodium carboxymethyl starch and bridged polyvinyl pyrrolidone), stabilizers (e.g., paraoxybenzoates, such as methylparaben and propylparaben; alcohols, such as chlorobutanol, benzyl alcohol and phenylethyl alcohol; benzalkonium chloride; phenols, such as phenol and cresol; thimerosal; dehydroacetic acid; and sorbic acid), corrigents (e.g., sweeteners, vinegars and perfumes) and diluents.

The dose varies, depending on many factors, including the condition and age of the patients, the severity and nature of the disorder and the route of administration. For example, in the case of oral administration, it is desirable to administer 0.01 mg/kg (preferably 0.1 mg/kg) as a lower limit and 50 mg/kg (preferably 10 mg/kg) as an upper limit for an adult per day, in a single dose or in divided doses, depending on the symptoms. In the case of intravenous administration, it is desirable to administer 0.001 mg/kg (preferably 0.01 mg/kg) as a lower limit and 10 mg/kg (preferably 5 mg/kg) as an upper limit for an adult, in a single dose or in divided doses, depending on the symptoms.

The present invention is further illustrated by the following non-limiting Examples and Formulation examples.

EXAMPLE 1

Test of Anticachexia Effects in Mice bearing Mouse Colon Cancer Colon 26 Cells

The test animals were CDF1 mice (females, 8 weeks old). They were employed in groups of 10 for each test. $1 \times 10^6$ mouse colon cancer Colon 26 cells were transplanted subcutaneously into each animal.

The test compounds were Compounds No. 1–94 and 2–78 as shown above in Tables 1 and 2, respectively, and having the following formulae:

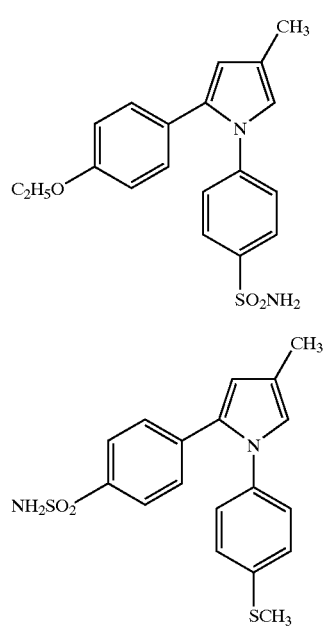

Compound No. 2-78

Compound No. 1-94

Each test compound was suspended in sterilized distilled water containing 0.5% w/v carboxymethyl cellulose (CMC) and administered orally once per day starting on the day of the tumor cell transplantation.

Each test animal was weighed immediately after tumor cell transplantation, and the weight (A g) was recorded. Each animal was then weighed on day 19 after tumor cell transplantation, and the weight (B g) was recorded. The weight gain on day 19 after tumor cell transplantation was calculated as B-A=$\Delta g_t$ for the test animals. The experiment was repeated with two control groups: the first control group (control group 1) was transplanted with the tumor cells but were not treated with any test compound, and the weight gain is reported as $\Delta g_{c1}$; the second control group (control group 2) were not transplanted with the tumor cells and were not treated with any test compound, and the weight gain is reported as $\Delta g_{c2}$. The body weight recovery rate was determined according to the following formula based on the weight gain on day 19 after tumor cell transplantation, and this value was used as an indicator of the anticachexia effect.

Body weight recovery rate (%)=($\Delta g_t$−$\Delta g_{c1}$)/($\Delta g_{c2}$−$\Delta g_{c1}$)×100

The results are shown in Table 3 below.

TABLE 3

| Administered Compound | Dose (mg/kg) | Weight Gain ($\Delta g$) | Body Weight Recovery Rate (%) |
|---|---|---|---|
| Compound 2–78 | 10 | 2.6 | 88 |
| Compound 2–78 | 3 | 2.5 | 85 |
| Compound 2–78 | 1 | 2.5 | 85 |
| Compound 1–94 | 10 | 3.1 | 98 |
| Compound 1–94 | 3 | 2.7 | 89 |
| Compound 1–94 | 1 | 2.2 | 78 |
| control group 1 | — | −1.4 | 0 |
| control group 2 | — | 3.2 | 100 |

It is clear from the above results that these compounds inhibited mouse tumor cachexia and reduced weight loss.

EXAMPLE 2

Test of Anticachexia Effects in Mice bearing Mouse Colon Cancer Colon 26 Cells

The procedure described in Example 1 was repeated, but using the compound of formula (III) as the test compound, and comparing the weight gain ($\Delta g_t$) of the test group of animals to which the compound of formula (III) had been administered with a control group ($\Delta g_c$) into which the tumor cells had been transplanted but to which no anti-tumor compound had been administered. The test animals were female CDF1 mice, 16 weeks old. Also, the weight gain was measured 22 days after tumor transplantation. The average body weight of each group of animals immediately after tumor transplantation was 25 to 26 g. The results are shown in Table 4.

TABLE 4

| Compound | Dose (mg/kg) | Average Weight Gain ($\Delta g$) |
|---|---|---|
| Compound (III) | 10 | 0.9 |
| Compound (III) | 3 | 0.3 |
| Compound (III) | 1 | 0.0 |
| None (Control group) | — | −4.2 |

It is clear from the above results that the compound of formula (III) inhibited mouse tumor cachexia and reduced weight loss.

EXAMPLE 3
Test of Anticachexia Effects in Mice bearing Mouse Colon Cancer Colon 26 Cells The procedure described in Example 2 was repeated, but using the compound of formula (IV) as the test compound, and comparing the weight gain ($\Delta g_t$) of the test group of animals to which the compound of formula (IV) had been administered with a control group ($\Delta g_c$) into which the tumor cells had been transplanted but to which no anti-tumor compound had been administered. The test animals were female CDF1 mice, 7 weeks old. Also, the weight gain was measured 15 days after tumor transplantation. The average body weight of each group of animals immediately after tumor transplantation was 20 to 21 g. The results are shown in Table 5.

TABLE 5

| Compound | Dose (mg/kg) | Average Weight Gain ($\Delta g$) |
|---|---|---|
| Compound (IV) | 10 | −0.6 |
| Compound (IV) | 3 | −1.3 |
| Compound (IV) | 1 | −1.2 |
| None (Control group) | — | −3.4 |

It is clear from the above results that the compound of formula (IV) inhibited mouse tumor cachexia and reduced weight loss.

EXAMPLE 4
Test of Anticachexia Effects in Mice bearing Mouse Colon Cancer Colon 26 Cells Test compounds [the compounds of formula (V), (VI), (VII), (VIII), (IX), (X), (XI), (XII), (XIII) and (XIV)] are administered in the same manner as described in Example 2. These compounds inhibit mouse tumor cachexia and recover loss of average of body weight.

EXAMPLE 5
Life-prolonging Activity Test

Observation of the mice used in Example 1 above was continued. The life-prolonging index was determined, based on the number of days each mouse survived, and this value was then used as an indicator of the life-prolonging effects of the test compounds.

It should be noted that, in the case of the group of mice treated with a test compound, oral administration of the respective compound once daily was continued on day 20 after tumor cell transplantation and beyond as well.

Life-prolonging index $(\%)=(S_t/S_c-1)\times 100$ $S_t$: Median value of survival time (days) of the group of mice treated with a test compound
$S_c$: Median value of survival time (days) of the control group which were not transplanted with tumor cells.

The results are shown in Table 6.

TABLE 6

| Compound Name | Dose (mg/kg) | Survival Period (median: days) | Life-prolonging Index (%) |
|---|---|---|---|
| Compound 2–78 | 10 | 48.5 | 67 |
| Compound 2–78 | 3 | 50.5 | 74 |
| Compound 2–78 | 1 | 45.0 | 55 |
| Compound 1–94 | 10 | 45.0 | 55 |
| Compound 1–94 | 3 | 35.0 | 21 |
| Compound 1–94 | 1 | 48.5 | 67 |
| None | — | 29.0 | 0 |

As is clear from Table 6, the compounds of the present invention exhibited a prominent life-prolonging effect.

EXAMPLE 6
Life-Prolonging Activity Test

The experiment reported in Example 5 was repeated with the animals used in Example 2. In the case of the group of mice treated with a test compound, oral administration of the respective compound once daily was continued on day 23 after tumor cell transplantation and beyond as well. The results are shown in Table 7.

TABLE 7

| Compound Name | Dose (mg/kg) | Survival Period (median: days) | Life-prolonging Index (%) |
|---|---|---|---|
| Compound (III) | 10 | 43.5 | 91 |
| Compound (III) | 3 | 37.5 | 63 |
| Compound (III) | 1 | 40.5 | 76 |
| None | — | 23.0 | — |

EXAMPLE 7
Life-Prolonging Activity

The experiment reported in Example 5 is repeated with the animals used in Examples 3 and 4. The compounds of formulae (IV), (V), (VI), (VII), (VIII), (IX), (X), (XI), (XII), (XIII) and (XIV) all inhibit mouse tumor cachexia and exhibit pronounced life-prolongation.

EXAMPLE 8
Test of Concomitant Use of Antitumor Agent

Mouse colon cancer cells are transplanted into CDF1 mice in the same manner as Example 1 followed by administration of the test compounds [Compound Nos. 2–78 and 1–94, and the compounds of formulae (III), (IV), (V), (VI), (VII), (VIII), (IX), (X), (XI), (XII), (XIII) and (XIV)] and an antitumor agent (5-fluorouracil or cisplatin).

The concomitant use of one of the compounds of the present invention and an antitumor agent remarkably inhibits tumor growth and cachexia, to afford a pronounced life-prolonging effect.

EXAMPLE 9
Inhibitory Effect on Lung Metastasis of Mouse Malignant Melanoma B16-BL6 Cells Groups of mice, each group containing ten C57BL/6 mice (female, age: 8 weeks) were transplanted intravenously into the tail vein with $3\times 10^4$ of mouse malignant melanoma B16-BL6 cells.

The mice were, when necessary, administered intravenously into the tail vein with a bacterial lipopolysaccharide (LPS) in an amount of 3 μg each within one hour before transplantation of the melanoma cells so as to accelerate lung metastasis of the melanoma [M. J. Anasagasti et al., J. Natl. Cancer Research, 89, 645–651 (1997).]

As test compounds, Compound No. 2–118, a compound of formula (IV), a compound of formula (V) and indomethacin were employed, and each was suspended in sterilized distilled water containing 0.5% w/v of carboxymethyl cellulose (CMC), and the suspensions were orally administered at a dose of 1 mg/kg per day for five days starting from the day of the melanoma cell transplantation.

Compound No. 2–118 is 2-(3,4-dimethylphenyl)-4-methyl-1-(4-sulfamoylphenyl)pyrrole.

Inhibitory activities on lung metastasis of the melanoma cells were evaluated in terms of the lung metastasis inhibitory rate (LMI %) by counting the number of metastatic colonies in the lung on the 10th day after intravenous transplantation of the mouse malignant melanoma B16-BL6 cells at the tail.

$$LMI(\%)=(1-N_t/N_c)\times 100$$

$N_t$: Numbers of lung metastatic colonies on the 10th day in groups administered with the test compounds; and
$N_c$: Numbers of lung metastatic colonies on the 10th day in control groups which were not administered with the test compounds.

The results are shown in Table 8.

TABLE 8

| Test compound | LPS administration | Dose (mg/kg) | LMI (%) |
|---|---|---|---|
| Compound 2–118 | No | 1 | 64 |
| Compound 2–118 | Yes | 1 | 34 |
| Compound (IV) | Yes | 1 | 9 |
| Compound (V) | Yes | 1 | 1 |
| Indomethacin | Yes | 1 | −1 |

It is clear from Table 8 that the present composition was successful in inhibiting metastasis of the mouse malignant melanoma B16-BL6 cells to the lung whether or not lung metastasis was accelerated by the LPS administration (induction of inflammation reaction).

In particular, the present composition showed a marked inhibition of lung metastasis, while the compound of formula (IV) and the compound of formula (V), which are COX-2-selective inhibitors, and indomethacin, which is a typical NSAID, had no such inhibitory activity under the lung metastasis accelerating conditions caused by inducing inflammatory reaction (as reflecting acceleration of metastasis of tumor in a surgical operation of resecting a tumor).

EXAMPLE 10

Antitumor Effect Against Mouse Sarcoma S-180 Cells $1\times10^6$ mouse sarcoma S-180 cells were transplanted subcutaneously in Balb/c nude mice (females, 8 weeks old) in groups of 10 each.

The test compound, Compound No. 2–118, was suspended in sterilized distilled water containing 0.5% w/v carboxymethyl cellulose (CMC) and administered orally once per day for 5 days starting on the day the tumor cells were transplanted.

Antitumor activity was assessed according to the following equation to determine the tumor growth inhibitory rate (GI %) on day 7 after the transplantation.

$$GI(\%)=(1-V_t/V_c)\times 100$$

$V_t$: Mean tumor volume on day 7 in a group administered test compound (*)
$V_c$: Mean tumor volume on day 7 in an untreated control group (*)
  *: Tumor volume is defined as ½×[tumor long axis]× [tumor short axis]2

The results are shown in Table 9.

TABLE 9

| Test Compound | Dose (mg/kg) | GI (%) |
|---|---|---|
| Compound 2–118 | 1 | 54 |

It is clear from Table 9 that the composition of the present application inhibited the growth of mouse tumor cells.

EXAMPLE 11

Antitumor Effect Against Human Colon Cancer KM12-HX Cells

Human colon cancer KM12-HX cells were orthotopically transplanted into the cecum of nude mice according to the method of Fu et al. [X. Fu et al., Anticancer Res., 12 (1992)] using Balb/c nude mice (females, 7 weeks old) in groups of 10 each. Specifically, an incision was made into the left lower abdominal region of each mouse under Abacin anesthesia, after which a thin section of tumor measuring 5 mm on a side was sutured to the cecum using absorbable surgical sutures to perform orthotopic transplant. The incision was sutured using absorbable surgical sutures and the mice were warmed and promptly awakened from anesthesia.

The test compound was suspended in sterilized distilled water containing 0.5% w/v carboxymethyl cellulose (CMC) and administered orally in a total of 9 doses consisting of one dose per day from days 3 to 7 after the tumor cell transplantation and from days 10 to 13 after the transplantation.

Antitumor activity was assessed according to the following equation to determine the tumor weight inhibitory rate (GI %) on day 14 after the transplantation.

$$GI(\%)=(1-V_t'/V_c')\times 100$$

$V_t'$: Mean tumor weight on day 14 in the group administered the test compound
$V_c'$: Mean tumor weight on day 14 in an untreated control group The results are shown in Table 10.

TABLE 10

| Test Compound | Dose (mg/kg) | GI (%) |
|---|---|---|
| Compound 2–118 | 0.3 | 12 |
| Compound 2–118 | 1 | 35 |
| Compound 2–118 | 3 | 45 |
| Compound 2–118 | 10 | 59 |

It is clear from Table 10 that the composition of the present invention inhibited the growth of human colon cancer cells at the orthotopic transplantation site.

Preparation of pharmaceutical formulations containing the compounds of the present invention is further illustrated by the following non-limiting Formulation Examples.

FORMULATION EXAMPLE 1

Capsules

A mixture of a compound of the present invention, such as the compound of formula (III), Compound No. 1–94, 2–78 or 2–118, is prepared in a digestive oily substance, such as soybean oil, cottonseed oil or olive oil, and filled into gelatin with a positive replacement pump to obtain soft capsules containing 100 mg of active ingredient. The resulting capsules are then washed and dried.

FORMULATION EXAMPLE 2

Tablets

Tablets are manufactured in accordance with conventional methods using 1100 mg of a compound of the present invention, such as the compound of formula (III), Compound No. 1–94, 2–78 or 2–118, 0.2 mg of colloidal silicon dioxide, 5 mg of magnesium stearate, 275 mg of microcrystalline cellulose, 11 mg of starch and 98.8 mg of lactose.

In this case, the tablets can be coated with a preparation coating if desired.

FORMULATION EXAMPLE 3

Injections 1.5% by weight of a compound of the present invention, such as the compound of formula (III), Compound No. 1–94, 2–78 or 2–118, is stirred in 10% by volume of propylene glycol, and is then adjusted to a constant volume by the addition of water for injection, after which it was sterilized to prepare injections.

FORMULATION EXAMPLE 4

Suspensions

A suspension is produced so as to contain 100 mg of a compound of the present invention, such as the compound of formula (III), Compound No. 1–94, 2–78 or 2–118, which is ground into a fine powder, 100 mg of sodium carboxymethyl cellulose, mg of sodium benzoate, 1.0 g of sorbitol solution (Japanese Pharmacopoeia) and 0.025 ml of vanillin in 5 ml of the suspension.

We claim:

1. A method for the treatment of tumor-related disorders in a mammal in need of such treatment, which method comprises administering to said mammal an effective amount of an active compound selected from the group consisting of 2-(4-ethoxyphenyl)-4-methyl-1-(4-sulfamoylphenyl)pyrrole and 4-methyl-1-(4-methylthiophenyl)-2-(4-sulfamoylphenyl)pyrrole.

2. The method of claim 1 for the treatment of tumor related disorders wherein the active compound is 4-methyl-1-(4-methylthiophenyl)-2-(4-sulfamoylphenyl)pyrrole.

3. The method of claim 1 for the treatment of tumor related disorders wherein the active compound is 2-(4-ethoxyphenyl)-4-methyl-1-(4-sulfamoylphenyl)pyrrole.

4. The method of claim 1 for the treatment of tumor-related disorders wherein the active compound is 4-methyl-1-(4-methylthiophenyl)-2-(4-sulfamoylphenyl)pyrrole.

5. The method of claim 1 for the treatment of tumor-related disorders wherein the active compound is 2-(4-ethoxyphenyl)-4-methyl-1-(4-sulfamoylphenyl)pyrrole.

6. The method of claim 1 for the treatment of tumor related disorder wherein the tumor related disorder is cachexia.

7. The method of claim 6 for the treatment of cachexia wherein the active compound is 4-methyl-1-(4-methylthiophenyl)-2-(4-sulfamoylphenyl)pyrrole.

8. The method of claim 6 for the treatment of cachexia wherein the active compound is 2-(4-ethoxyphenyl)-4-methyl-1-(4-sulfamoylphenyl)pyrrole.

* * * * *

UNITED STATES PATENT AND TRADEMARK OFFICE
CERTIFICATE OF CORRECTION

PATENT NO.        : 6,887,893 B1
APPLICATION NO. : 09/212556
DATED             : May 3, 2005
INVENTOR(S)      : Kurakata et al.

It is certified that error appears in the above-identified patent and that said Letters Patent is hereby corrected as shown below:

Title Page, Left Column, (56) References Cited, under U.S. PATENT DOCUMENTS insert

| | | |
|---|---|---|
| -- 4,962,119 | 10/1990 | Boschelli et al |
| 5,466,823 | 11/1995 | Talley et al |
| 5,550,142 | 8/1996 | Ducharme et al |
| 5,972,986 | 10/1999 | Seibert et al --; | under FOREIGN PATENT DOCUMENTS insert

| | | | |
|---|---|---|---|
| -- EP | 0688723 | A1 | 10/1997 |
| EP | 0745596 | A | 12/1996 |
| EP | 0863134 | A | 9/1998 |
| WO | WO 92/10190 | | 6/1992 |
| WO | WO 92/10498 | | 6/1992 |
| WO | WO 94/13635 | | 6/1994 |
| WO | WO 95/18799 | | 7/1995 |
| WO | WO 95/32194 | | 11/1995 |
| WO | WO 98/06708 | | 2/1998 --; | under OTHER PUBLICATIONS insert

-- * Strelkov et al, "Effects of systemic . . .", *Am. J. Physiol.*, vol. 257, pp. C261-67, (1989).

J.J. Li et al, "1,2-Diarylcyclopentenes as selective cyclooxygenase-2 inhibitors and orally active anti-inflammatory agents", *Journal of Medicinal Chemistry*, vol. 38, No. 22, pp. 4570-4578 (Oct. 1995).

N. Futaki et al, "NS-398, A new anti-inflammatory agent, selectively inhibits prostaglandin G/H synthase/cyclooxygenase (COX–2) activity in vitro", *Prostaglandins*, vol. 47, pp. 55-59 (Jan 1994).

K. Tanaka et al, "T-614, A novel antirheumatic drag, inhibits both the activity and induction of cyclooxygenase-2 (COX-2) in cultured fibroblasts", *Japanese Journal of Pharmacology,* vol. 67, No. 4, pp. 305-314 (April 1995).

UNITED STATES PATENT AND TRADEMARK OFFICE
CERTIFICATE OF CORRECTION

PATENT NO. : 6,887,893 B1
APPLICATION NO. : 09/212556
DATED : May 3, 2005
INVENTOR(S) : Kurakata et al.

It is certified that error appears in the above-identified patent and that said Letters Patent is hereby corrected as shown below:

Oshima et al, "Suppression of intestinal polyposis in $Apc^{\Delta 716}$ knockout mice by inhibition of cyclooxygenase 2 (COX-2)", *Cell,* vol. 87, pp. 803-809, (November 29, 1996).

Teicher et al, "Cyclooxygenase and lipoxygenase inhibitors as modulators of cancer therapies", *Cancer Chemother Pharmacol,* vol. 33, pp. 515-522 (1994).

Tsujii M. et al, "Cyclooxygenase-2 expression in human colon cancer cells increases metastatic potential", Proc. Natl. Acad. Sci. USA 1997, April 1; 94(7), B9533, 36-40, Abstract, Medline (on-line) Department of Medicine USA, No. 97250538.

Ristimakia et al, "Expression of cyclooxygenase-2 in human gastric carcinoma", Cancer, Res., 1997 April 1; 57 (7), 1276-80, Abstract, Medline (on-line) Department of Medicine USA. --.

\* Cited by Examiner

Column 34, lines 15-17 (Claim 4) : Delete in entirety.

Column 34, lines 18-20 (Claim 5) : Delete in entirety.

Signed and Sealed this

Twenty-fifth Day of March, 2008

JON W. DUDAS
*Director of the United States Patent and Trademark Office*